US009656973B2

(12) United States Patent
McCarthy

(10) Patent No.: US 9,656,973 B2
(45) Date of Patent: *May 23, 2017

(54) PROCESSES FOR PREPARING LINEZOLID

(71) Applicant: Indiana University Research and Technology Corporation, Indianapolis, IN (US)

(72) Inventor: James R. McCarthy, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/862,841

(22) Filed: Sep. 23, 2015

(65) Prior Publication Data
US 2016/0024032 A1    Jan. 28, 2016

Related U.S. Application Data

(63) Continuation of application No. 13/695,211, filed as application No. PCT/US2011/034278 on Apr. 28, 2011, now Pat. No. 9,206,141.

(60) Provisional application No. 61/329,892, filed on Apr. 30, 2010, provisional application No. 61/359,851, filed on Jun. 30, 2010, provisional application No. 61/375,576, filed on Aug. 20, 2010, provisional application No. 61/389,534, filed on Oct. 4, 2010, provisional application No. 61/421,442, filed on Dec. 9, 2010.

(51) Int. Cl.
*C07D 263/20* (2006.01)
*C07D 263/22* (2006.01)
*C07D 295/00* (2006.01)
*C07D 413/10* (2006.01)

(52) U.S. Cl.
CPC ................ *C07D 263/20* (2013.01)

(58) Field of Classification Search
CPC .. C07D 263/22; C07D 295/00; C07D 413/10; C07D 263/20; A61K 31/421; A61K 31/422; A61K 31/5377
USPC ......... 548/230, 229; 544/137; 514/376, 236; 549/551
See application file for complete search history.

(56) References Cited

U.S. PATENT DOCUMENTS

| 3,725,450 | A | 4/1973 | Coury et al. |
| 4,937,331 | A | 6/1990 | Evans |
| 5,278,179 | A | 1/1994 | Elbe et al. |
| 5,756,834 | A | 5/1998 | Pasenok et al. |
| 6,444,813 | B2 | 9/2002 | Bergren |
| 7,271,171 | B2 | 9/2007 | Baraldi et al. |
| 9,206,141 | B2 * | 12/2015 | McCarthy ............ C07D 263/20 |
| 2002/0032348 | A1 | 3/2002 | Pearlman |
| 2002/0086900 | A1 | 7/2002 | Perrault et al. |
| 2003/0100608 | A1 | 5/2003 | Cirillo et al. |
| 2008/0045708 | A1 | 2/2008 | Tian |

FOREIGN PATENT DOCUMENTS

| CN | 101 220 001 | 7/2008 |
| CN | 101 638 392 | 2/2010 |
| TW | 200808782 | 2/2008 |
| WO | WO 95/23797 | 9/1995 |
| WO | WO 99/24393 | 5/1999 |
| WO | WO 01/57035 | 8/2001 |
| WO | WO/01/87865 | 11/2001 |
| WO | WO 2005/099353 | 10/2005 |
| WO | WO 2006/008754 | 1/2006 |
| WO | WO 2006/091731 | 8/2006 |
| WO | WO 2006/091848 | 8/2006 |
| WO | WO 2007/116284 | 10/2007 |

OTHER PUBLICATIONS

Supplementary European Search Report and European Search Opinion for Application No. 11 77 5554, dated Sep. 18, 2013.
Zhang, X., et al, "An efficient and practical synthesis of antibacterial linezolid," 2009, Journal of Chemical Research, 12, 739-740.
Xu, G., et al., "A convenient synthesis of oxazolidinone derivatives linezolid and eperezolid from (S)-glyceraldehyde acetonide," 2008, Heteroatom Chemistry, 19, 316-319.
Madhusudhan, G., et al,. "Stereoselective synthesis of novel (R)- and (S)-5-azidomethyl-2-oxazolidinones from (5)-epichlorohydrin: a key precursor for the oxazolidinone class of antibacterial agents," 2008, Tetrahedron Letters, 49(19), 3060-3062.
Narina, S. V., et al., "Short and practical enantioselective synthesis of linezolid and eperezolid via proline-catalyzed asymmetric α-aminooxylation," 2006, Tetrahedron Letters, 47(38), 6799-6802.
Lohray, B. B., Baskaran, S., Srinivasa Rao, B., Yadi Reddy, B., & Nageswara Rao, I. (1999). A short synthesis of oxazolidinone derivatives linezolid and eperezolid: a new class of antibacterials. *Tetrahedron letters*, 40(26), 4855-4856.
Sridhar, R., & Perumal, P. T. (2003). Synthesis of acyl azides using the Vilsmeier complex. *Synthetic communications*, 33(4), 607-611.
Maccaroni, E., et al., "Polymorphism of linezolid: A combined single-crystal, powder diffraction and NMR study," 2008, International Journal of Pharmaceutics, 351(1), 144-151.
PCT International Search Report and Written Opinion completed by the ISA/US on Jun. 26, 2011 and issued in Connection with PCT/US2011/034278.
Brickner, S. J., et al. "Synthesis and antibacterial activity of U-100592 and U-100766, two oxazolidinone antibacterial agents for the potential treatment of multidrug-resistant gram-positive bacterial infections," 1996, Journal of Medicinal Chemistry, 39, 673-679.
Li et al., Contemporary Drug synthesis, John Wiley & Sons, pp. 1-221, 2004, ISBN 0-471-21480-9, Chapter 7, Antibacterials: Ciprofloxacin and Linezolid, see p. 84-85.

(Continued)

*Primary Examiner* — Alicia L Otton
*Assistant Examiner* — Sagar Patel
(74) *Attorney, Agent, or Firm* — Barnes & Thornburg LLP

(57) ABSTRACT

Processes and intermediates for preparing linezolid, and pharmaceutically acceptable salts thereof, are described herein.

20 Claims, No Drawings

(56) References Cited

OTHER PUBLICATIONS

Cotarca et al., Phosgenations—A Handbook, Wiley-VCH Verlag GbmH & Co., pp. 1-656, 2003, ISBN 3-527-29823-1, Chapter 4, Phosgenation Reactions, see p. 92.
Fujisaki, F., N. be, and K. Sumoto, "A new Route for the synthesis of Linezolid mimetic 3,4-disubstituted Oxazolidin-2-One derivatives," 2008, Heterocycles, 75(7), 1681-1694.
Pang, H. et al., "Synthesis of (R)-3-(3-Fluoro-4-morpholinylphenyl)-2-oxo-5-oxazolidinylmethanol," Fine Chemicals, 2004, 21, 70-71, 75. (Abstract Only).
Gregory, W. A. et al., "Antibacterials. Synthesis and structure-activity studies of 3-aryl-2-oxooxazolidines. 2. The 'A' group," 1990, *J. Med. Chem.*, 33, 2569-2578.
Extended European Search Report prepared for European Patent Application No. 14197369.3, mailed Aug. 3, 2015.

\* cited by examiner

PROCESSES FOR PREPARING LINEZOLID

This application is a continuation of U.S. application Ser. No. 13/695,211 filed on Oct. 29, 2012, which is a U.S. national counterpart application of international application serial No. PCT/US2011/034278, filed Apr. 28, 2011, which claims the benefit of U.S. Provisional Application Nos. 61/329,892 filed Apr. 30, 2010, 61/359,851 filed Jun. 30, 2010, 61/375,576 filed Aug. 20, 2010, 61/389,534 filed Oct. 4, 2010, and 61/421,442 filed Dec. 9, 2010. The entire disclosures of U.S. application Ser. No. 13/695,211, PCT/US2011/034278, U.S. Provisional Patent Application Nos. 61/329,892, 61/359,851, 61/375,576, 61/389,534, and 61/421,442 are herein incorporated by reference.

TECHNICAL FIELD

The invention described herein pertains to processes for preparing linezolid, and pharmaceutically acceptable salts thereof.

BACKGROUND AND SUMMARY OF THE INVENTION

Linezolid is a synthetic antibiotic used for the treatment of serious infections caused by Gram-positive bacteria that are resistant to several other antibiotics. A member of the oxazolidinone class of drugs, linezolid is active against most Gram-positive bacteria that cause disease, including streptococci, vancomycin-resistant enterococci (VRE), and methicillin-resistant Staphylococcus aureus (MRSA). The main indications of linezolid are infections of the skin and soft tissues and pneumonia (particularly hospital-acquired pneumonia), although off-label use for a variety of other infections is becoming popular. Linezolid is marketed by Pfizer under the trade names Zyvox™ (in the United States, United Kingdom, Australia, and several other countries), Zyvoxid™ (in Europe), and Zyvoxam™ (in Canada and Mexico). The current sales for linezolid are over one billion US dollars per year and rising in part because of its indication for the treatment of many forms of MRSA. Linezolid is quite expensive, as a course of treatment can cost up to several thousand U.S. dollars. Much of the high cost of linezolid has been attributed to the expense of its manufacture. Therefore, the development of new, more economical processes for manufacturing linezolid and pharmaceutically acceptable salts thereof are needed.

Described herein are efficient processes for the preparation of linezolid and pharmaceutically acceptable salts thereof. In one embodiment, the processes described herein include the step of preparing the oxazolidinone present in linezolid and pharmaceutically acceptable salts thereof from an oxirane and an isocyanate.

In another alternative aspect, the processes include the step of preparing 3-fluoro-4-chloronitrobenzene from 4-chloronitrobenzene and fluorine. In another alternative aspect, the processes include the step of preparing 3-fluoro-4-(1-morpholino)nitrobenzene, or a salt thereof, from 3-fluoro-4-halonitrobenzene and morpholine. In another alternative aspect, the processes include the step of preparing 3-fluoro-4-(1-morpholino)aniline, or a salt thereof, from 3-fluoro-4-(1-morpholino)nitrobenzene and a reducing agent. In another alternative aspect, the processes include the step of preparing 3-fluoro-4-(1-morpholino)phenyl isocyanate from 3-fluoro-4-(1-morpholino)aniline and an acylating agent. In another alternative aspect, the processes include the step of preparing a compound of the formula

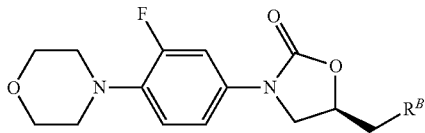

or a salt thereof from 3-fluoro-4-(1-morpholino)phenyl isocyanate and an oxirane of the formula

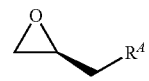

where $R^A$ is halo or a protected amino group; and $R^B$ is halo, amino, or a protected amino group. In another alternative aspect, the processes include the step of preparing a compound of the formula

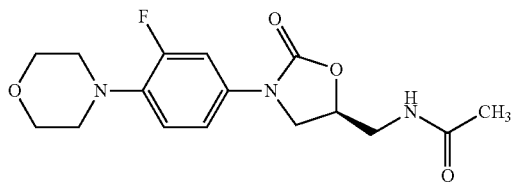

or a salt thereof from

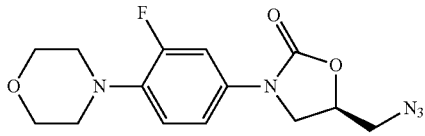

and $CH_3C(O)SH$.

In another embodiment, described herein are process that proceed in high overall yield. In another embodiment, described herein are process that do not require any purifications using chromatography. In another embodiment, described herein are process where the products from each step are isolated as solids and/or crystalline solids. In another embodiment, described herein are process that proceed with high enantiomeric excess. It is to be understood that the processes described herein may be performed using and to produce racemic material, or optically active material of either absolute configuration. It is also to be understood that the processes described herein may be routinely adapted to prepare any of a wide variety of materials having a predetermined enanatiomeric excess or a predetermined range of enanatiomeric excess.

DETAILED DESCRIPTION

In another embodiment, described herein is a process for preparing linezolid or a pharmaceutically acceptable salt thereof, the process comprising a step selected from the group consisting of
 (a) mixing 4-chloronitrobenzene with fluorine to prepare 3-fluoro-4-chloronitrobenzene;
 (b) mixing 3-fluoro-4-halonitrobenzene with morpholine to prepare 3-fluoro-4-(1-morpholino)nitrobenzene, or a salt thereof;

(c) mixing 3-fluoro-4-(1-morpholino)nitrobenzene with a reducing agent to prepare 3-fluoro-4-(1-morpholino)aniline, or a salt thereof;

(d) mixing 3-fluoro-4-(1-morpholino)aniline with an acylating agent to prepare 3-fluoro-4-(1-morpholino)phenyl isocyanate;

(e) mixing 3-fluoro-4-(1-morpholino)phenyl isocyanate with an oxirane of the formula

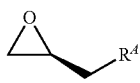

to prepare a compound of the formula

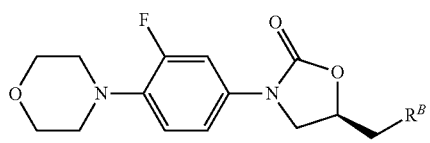

or a salt thereof; where $R^A$ is halo or a protected amino group; and $R^B$ is halo, amino, or a protected amino group; and (f) mixing a compound of the formula

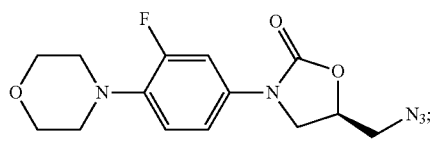 [SMILES: [N-]=[N+]=NC[C@H]1CN(c2ccc(N3CCOCC3)c(F)c2)C(=O)O1]

with $CH_3C(O)SH$ to prepare a compound of the formula

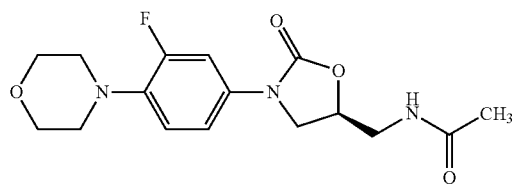 [SMILES: CC(=O)NC[C@H]1CN(c2ccc(N3CCOCC3)c(F)c2)C(=O)O1]

or a salt thereof;
and combinations thereof.

It is to be understood that in the foregoing embodiment, processes are described that include one or more of any of the steps, two or more of any of the steps, three or more of any of the steps, and so on. For example, processes are described herein that include step (e); processes are also described herein that include steps (d) and (e); processes are also described herein that include steps (e) and (f); processes are also described herein that include steps (d), (e), and (f); and so on.

It is also to be understood that in step (e) the $R^A$ group on the oxirane and the $R^B$ group on the oxazolidinone are generally the same. Illustratively, when $R^A$ is halo, such as chloro, $R^B$ is halo, such as chloro; and when $R^A$ is a protected amino group, $R^B$ is a protected amino group. However, it is also to be understood that $R^A$ may be converted to a different $R^B$ in step (e) and still fall within the scope of the process step. For example, when $R^A$ is halo, such as chloro, $R^B$ may be amino or a protected amino if other components are added to the mixture that are capable of concomitantly or sequentially converting the halo, such as chloro, to amino or a protected amino. Similarly, when $R^A$ is a protected amino, $R^B$ may be amino if other components are added to the mixture that are capable of concomitantly or sequentially converting the protected amino to amino.

In another embodiment, described herein is the process as in the preceding embodiment wherein the 3-fluoro-4-halonitrobenzene is 3,4-difluoronitrobenzene.

In another embodiment, described herein is the process as in any of the preceding embodiments wherein the 3-fluoro-4-halonitrobenzene is 4-chloro-3-fluoronitrobenzene.

In another embodiment, described herein is the process as in any of the preceding embodiments wherein the reducing agent is hydrogen gas.

In another embodiment, described herein is the process as in any of the preceding embodiments wherein the acylating agent is phosgene or a phosgene analog. Illustrative phosgene analogs include diphosphosgene, triphosgene, carbonyldiimidazole, and the like.

In another embodiment, described herein is the process as in any of the preceding embodiments, comprising step (e).

In another embodiment, described herein is a process for preparing linezolid or a pharmaceutically acceptable salt thereof, the process comprising a step selected from the group consisting of (a) mixing 3-fluoro-4-halobenzoic acid with morpholine to prepare 3-fluoro-4-(morpholino)benzoic acid, or a salt thereof;

(b) mixing 3-fluoro-4-(morpholino)benzoic acid with an activating agent to prepare the corresponding activated acid;

(c) mixing the corresponding activated acid of 3-fluoro-4-(morpholino)benzoic acid with an azide salt to prepare 3-fluoro-4-(morpholino)benzoyl azide, or a salt thereof;

(d) mixing 3-fluoro-4-(morpholino)benzoyl azide with an oxirane of the formula

to prepare a compound of the formula

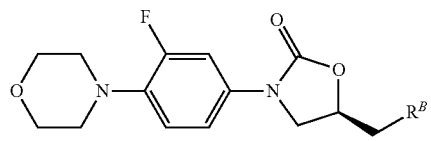

or a salt thereof; where $R^A$ is halo or a protected amino group; and $R^B$ is halo, amino, or a protected amino group;
and combinations thereof.

It is to be understood that in the foregoing embodiment, processes are described that include one or more of any of the steps, two or more of any of the steps, three or more of any of the steps, and so on. For example, processes are described herein that include step (d); processes are also described herein that include steps (c) and (d); processes are also described herein that include steps (b), (c), and (d); and so on.

It is also to be understood that in step (d) the $R^A$ group on the oxirane and the $R^B$ group on the oxazolidinone are generally the same. Illustratively, when $R^A$ is halo, such as chloro, $R^B$ is halo, such as chloro; and when $R^A$ is a protected amino group, $R^B$ is a protected amino group. However, it is also to be understood that $R^A$ may be converted to a different $R^B$ in step (d) and still fall within the scope of the process step. For example, when $R^A$ is halo, such as chloro, $R^B$ may be amino or a protected amino if other components are added to the mixture that are capable of concomitantly or sequentially converting the halo, such as chloro, to amino or a protected amino. Similarly, when $R^A$ is a protected amino, $R^B$ may be amino if other components are added to the mixture that are capable of concomitantly or sequentially converting the protected amino to amino.

In another embodiment, described herein is the process as in any of the preceding embodiments wherein the 3-fluoro-4-halobenzoic acid is 3,4-difluorobenzoic acid.

In another embodiment, described herein is the process as in any of the preceding embodiments wherein the 3-fluoro-4-halobenzoic acid is 4-chloro-3-fluorobenzoic acid.

In another embodiment, described herein is the process as in any of the preceding embodiments wherein the activating agent is a chlorinating agent and the activated acid is an acid chloride. It is to be understood that any of a wide variety of activating agents may be used, including but not limited to, brominating agents, pentafluorophenylating agents, peptide coupling agents, and the like.

In another embodiment, described herein is the process as in any of the preceding embodiments wherein the chlorinating agent comprises thionyl chloride, phosphoryl chloride, phosphorous pentachloride, and the like, or a combination thereof.

In another embodiment, described herein is the process as in any of the preceding embodiments wherein the chlorinating agent comprises phosphorous pentachloride.

In another embodiment, described herein is the process as in any of the preceding embodiments wherein steps (b) and (c) are performed contemporaneously. Illustratively, the activating agent is phosphoryl chloride, and the azide salt is sodium azide.

In another embodiment, described herein is the process as in any of the preceding embodiments comprising step (d).

In another embodiment, described herein is the process as in any of the preceding embodiments wherein the oxirane is a compound of the formula

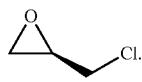

In another embodiment, described herein is the process as in any of the preceding embodiments wherein the oxirane is a compound of the formula

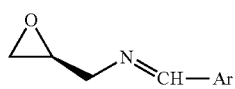

where Ar is optionally substituted phenyl.

In another embodiment, described herein is the process as in any of the preceding embodiments wherein Ar is phenyl.

In another embodiment, described herein is the process as in any of the preceding embodiments wherein Ar is 4-chlorophenyl.

In another embodiment, described herein is the process as in any of the preceding embodiments wherein $R^A$ is an imine.

In another embodiment, described herein is the process as in any of the preceding embodiments wherein $R^A$ is benzylidene amino, where the benzyl is optionally substituted.

In another embodiment, described herein is the process as in any of the preceding embodiments wherein $R^A$ is benzylidene amino, 4-chlorobenzylidene amino; 4-bromobenzylidene amino; or 2,4-dichlorobenzylidene amino.

In another embodiment, described herein is the process as in any of the preceding embodiments wherein $R^A$ is benzylidene amino.

In another embodiment, described herein is the process as in any of the preceding embodiments wherein $R^B$ is an imine.

In another embodiment, described herein is the process as in any of the preceding embodiments wherein $R^B$ is benzylidene amino, where the benzyl is optionally substituted.

In another embodiment, described herein is the process as in any of the preceding embodiments wherein $R^B$ is benzylidene amino, 4-chlorobenzylidene amino; 4-bromobenzylidene amino; or 2,4-dichlorobenzylidene amino.

In another embodiment, described herein is the process as in any of the preceding embodiments wherein $R^B$ is benzylidene amino.

In another embodiment, described herein is the process as in any of the preceding embodiments wherein the azide salt is sodium azide.

In another embodiment, described herein is a process for preparing a compound of the formula

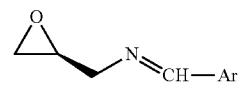

where Ar is optionally substituted phenyl;
the process comprising the step of mixing a compound of the formula

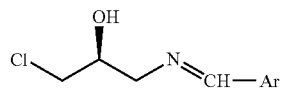

with a base.

In another embodiment, described herein is a compound of the formula

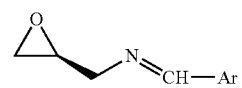

where Ar is optionally substituted phenyl.

In another embodiment, described herein is the process or compound of any of the preceding embodiments wherein Ar is phenyl.

In another embodiment, described herein is the process or compound of any of the preceding embodiments wherein Ar is 4-chlorophenyl.

In another embodiment, described herein is a process for preparing 3-fluoro-4-(1-morpholino)phenyl isocyanate, the process comprising the step of mixing 3-fluoro-4-(1-morpholino)aniline with an acylating agent.

In another embodiment, described herein is the process as in any of the preceding embodiments wherein the acylating agent is phosgene or a phosgene analog.

In another embodiment, described herein is a compound of the formula 3-fluoro-4-(1-morpholino)phenyl isocyanate.

In another embodiment, described herein is a process for preparing 3-fluoro-4-chloronitrobenzene, the process comprising the step of mixing 4-chloronitrobenzene with fluorine.

In another embodiment, described herein is a compound of the formula 3-fluoro-4-chloronitrobenzene.

In another embodiment, described herein is a process for preparing 3-fluoro-4-(morpholino)benzoyl azide, or a salt thereof, the process comprising the steps of (a) mixing 3-fluoro-4-(morpholino)benzoic acid with an activating agent to prepare the corresponding activated acid; and (b) mixing the corresponding activated acid with an azide salt.

In another embodiment, described herein is the process of the preceding embodiment wherein the activating agent is a chlorinating agent and the activated acid is an acid chloride.

In another embodiment, described herein is the process of any of the preceding embodiments wherein the chlorinating agent comprises thionyl chloride, phosphoryl chloride, phosphorous pentachloride, or a combination thereof.

In another embodiment, described herein is the process of the preceding embodiment wherein the chlorinating agent comprises phosphorous pentachloride.

In another embodiment, described herein is a compound of the formula 3-fluoro-4-(morpholino)benzoyl azide, or a salt thereof.

In another embodiment, described herein are efficient, convergent processes for preparation of the antibiotic Linezolid, and pharmaceutically acceptable salts thereof. In another illustrative embodiment, the processes include the following sequence of steps:

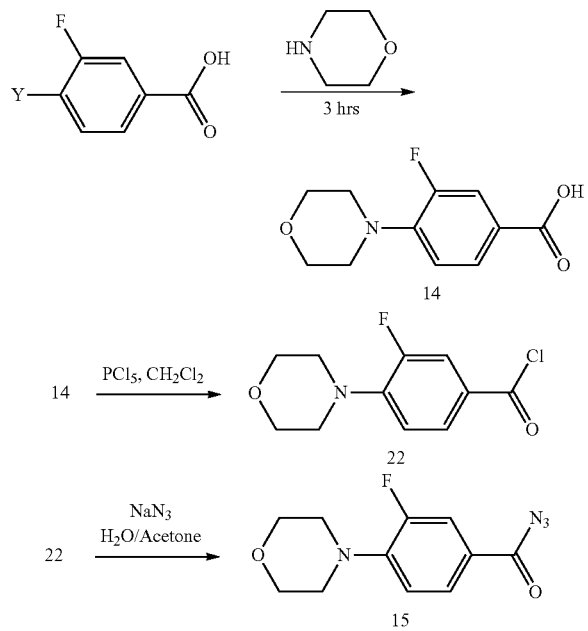

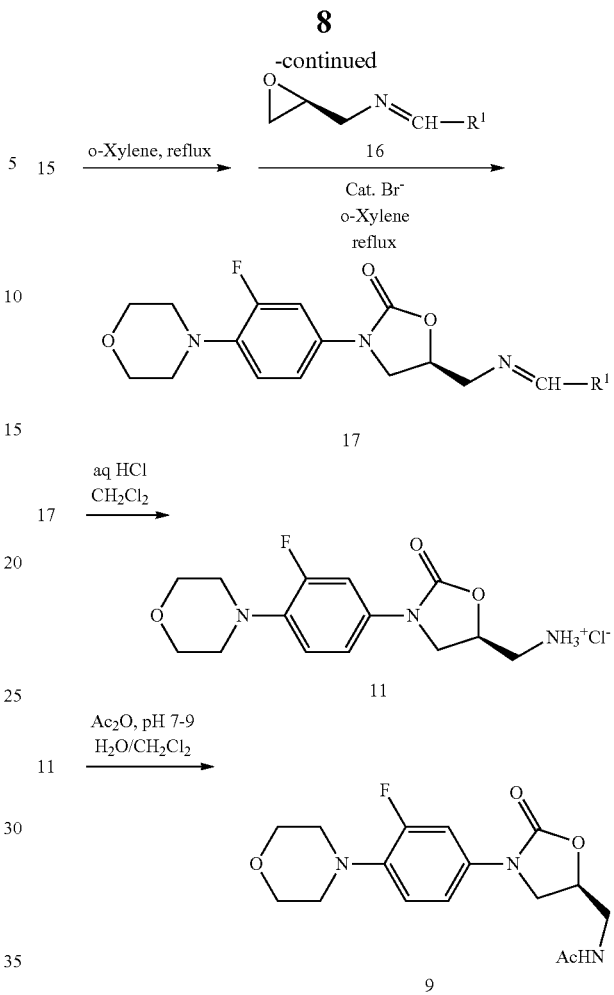

In one aspect of the processes, the substituent Y is a leaving group such as a halogen, and the like. Illustratively, Y is F or Cl. The preparation of compound (14) may be performed as a neat mixture or in a solvent, such as sulfolane. In another embodiment, compound (14) in the above scheme precipitates as a solid from the reaction mixture upon acidification, and may be optionally further purified by crystallization.

It is to be understood that a wide variety of solvent systems may be employed in each of the steps described herein. For example, in the conversion of compound (14) to compound (15), illustrative solvents include, but are not limited to, $CH_2Cl_2$, acetone/$H_2O$ mixtures, xylenes, xylene/$H_2O$ mixtures, DMF, DMSO, and the like. In one embodiment, intermediate acid chloride (22) is not isolated. In another embodiment, intermediate acid chloride (22) is isolated as a crystalline solid. In another embodiment, illustrative catalytic sources of $Br^-$ include, but are not limited to, magnesium bromide etherate, lithium bromide in combination with a phosphine oxide, such as tri-n-butylphosphine oxide, and the like.

In another embodiment, $R^1$ is alkyl, aryl or heteroaryl, each of which is optionally substituted. Illustratively, $R^1$ is optionally substituted phenyl, including but not limited to phenyl, 4-chlorophenyl, 2,4-dichlorophenyl, 2,6-dichlorophenyl, 4-bromophenyl, 4-nitrophenyl, and the like. Illustratively, $R^1$ is phenyl. In another embodiment, compound (17) in the above scheme precipitates or crystallizes from the reaction mixture, and may be optionally further purified by crystallization. It has been unexpectedly discovered that compound (17), when R¹ is unsubstituted phenyl, is also isolable from the reaction mixture as a solid. In another embodiment, compound (11) in the above scheme precipitates or crystallizes from the reaction mixture, and may be optionally further purified by crystallization. Without being bound by theory, it is believed herein that azide (15) in the processes described herein is converted to the corresponding isocyanate (6)

reaction mixture, and may be optionally further purified by crystallization. Compound (6) may be subsequently mixed with oxiranes (16) described herein, and carried forward to prepare linezolid, or a pharmaceutically acceptable salt thereof.

In another embodiment, described herein is a process for the conversion of acid azides, such as compound (15) and/or isocyanates, such as compound (6) into linezolid using epichlorohydrins. In another illustrative embodiment, the processes include the following sequence of steps:

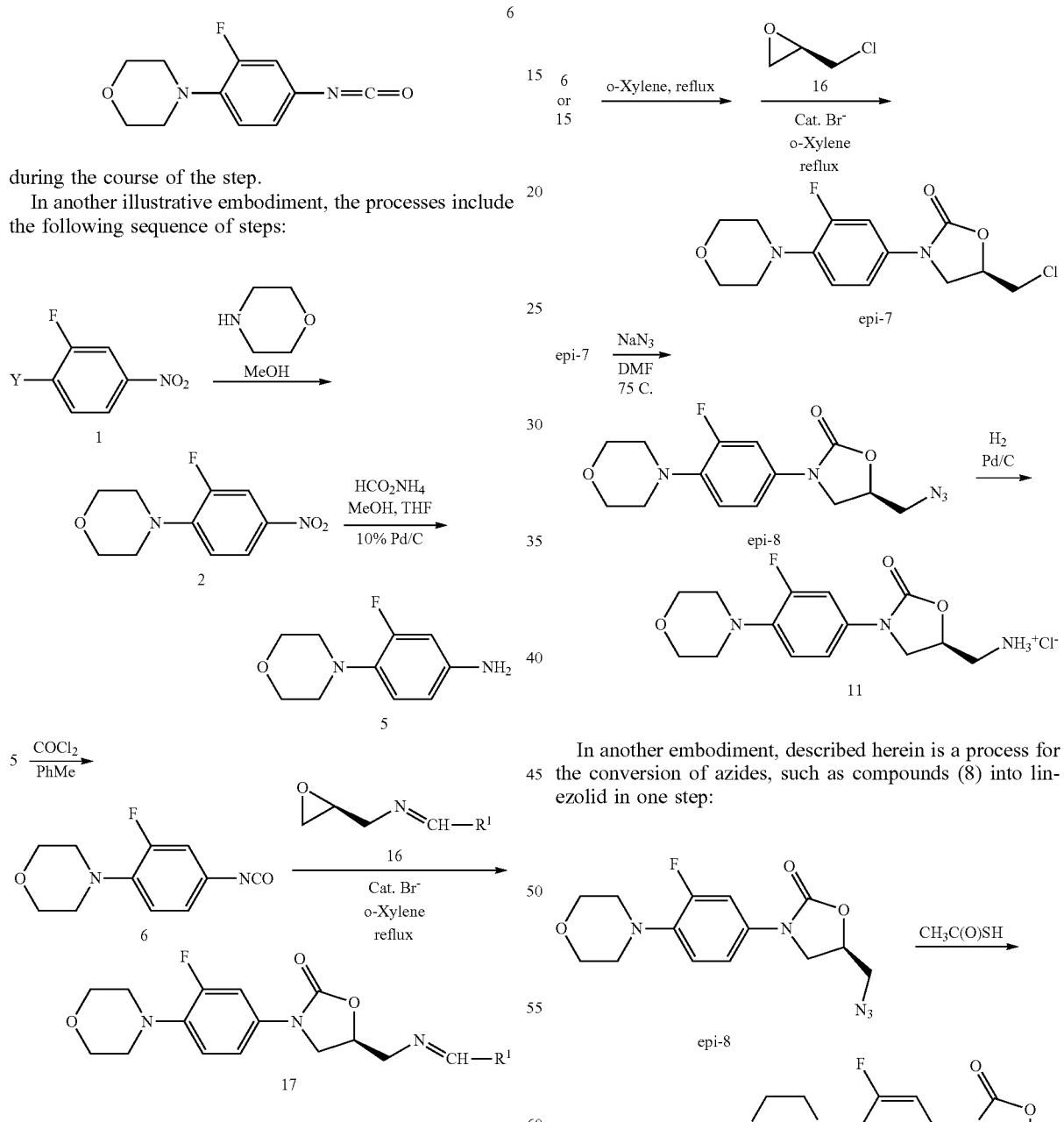

during the course of the step.

In another illustrative embodiment, the processes include the following sequence of steps:

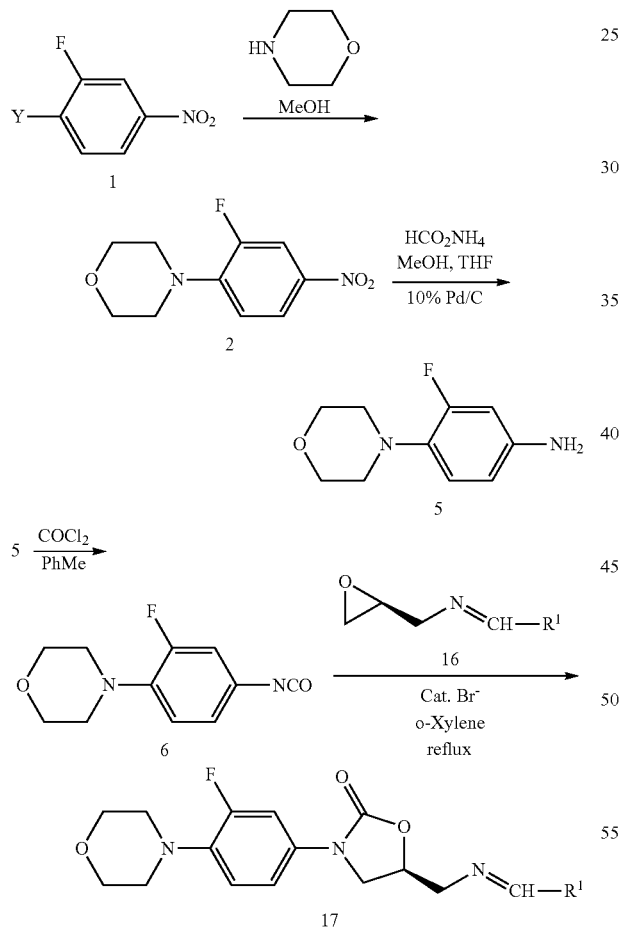

wherein the substituents Y are as defined above. In another illustrative embodiment, compound (2) crystallizes from the reaction mixture, and may be optionally further purified by crystallization. It is to be understood that a wide variety of reducing agents, including HCO₂NH₄ and catalytic Pd may be used in the processes described herein. In another illustrative embodiment, compound (6) crystallizes from the In another embodiment, described herein is a process for the conversion of azides, such as compounds (8) into linezolid in one step:

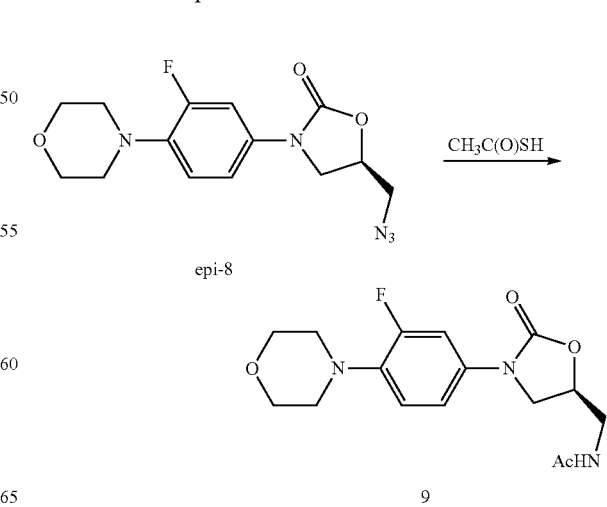

In another illustrative embodiment, imine or Schiff base epoxide intermediates such as those illustrated below for compound (16A), and processes for preparing them are described. Illustratively, compounds (16A) may be prepared as illustrated in the following scheme

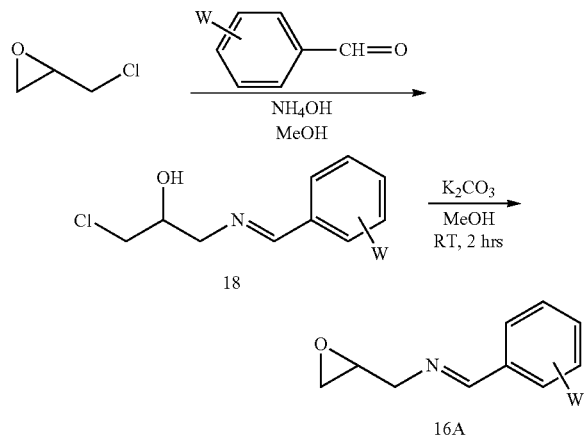

wherein W represents one or more substituents as described herein. It is to be understood that the imines described herein may be either in a (Z) or (E) configuration, or a wide variety of mixtures thereof. Without being bound by theory, it is believed herein that the arylalkylidene imines are typically in or predominantly in the (E) configuration, as shown herein for compounds such as (16A).

In another embodiment, described herein are processes for the preparation of 3-fluoro-4-(1-morpholino)nitrobenzene. In one aspect, the processes include the step of displacing a leaving group present at the 4-position on the corresponding 3-fluoronitrobenzene. Illustrative leaving groups include halogens, such as chloro and fluoro. 3,4-difluoronitrobenzene is commercially available. 4-chloro-3-fluoronitrobenzene may be prepared as described herein by fluorinating 4-chloronitrobenzene.

In another embodiment, described herein is a convergent process for the preparation of the antibiotic linezolid starting from 3,4-difluorobenzoic acid and (S)-epichlorohydrin. In one aspect, this convergent process provides linezolid in an overall yield of 34.7%. In another embodiment, processes described herein are used to prepare linezolid having an enantiomeric excess of about 97% or greater, about 98% or greater, or about 99% or greater. In another aspect, the processes described herein avoid the use of expensive reagents such as lithium t-butoxide and (R)-glycidyl butyrate.

EXAMPLES

The following examples further illustrate specific embodiments of the invention. However, the following examples should not be interpreted in any way to limit the invention.

Example 1

General. Products were analyzed by LCMS (dissolving the product in acetonitrile) under the following conditions. Column: Agilent Eclipse XDB-C18, 5 uM, 4.6×150 mm. Solvent A: 5 mM Ammonium acetate in Water. Solvent B: 5 mM Ammonium acetate in CH$_3$CN:MeOH (1:1). Method A: Time 0 Min: 20% B; Time 25 min 100% B; gradient elution flow rate 1.00 ml/min. Method B: Time 0 Min: 20% B; Time 10 min 100% B; stop time 12 min; gradient elution flow rate 1.00 ml/min. GCMS analyses were performed under the following conditions: Column: HP-5 5% phenyl methyl siloxane (HP1909/J-433). Method: Time 0 min 80° C.; Time 2 min column temp increases at 20° C./min to 300° C.; Stop Time 12 min.

Example 2

Fluorination of 4-chloronitrobenzene with fluorine gas in sulfuric acid provided 4-chloro-3-fluoronitrobenzene as a crystalline solid on aqueous workup of the reaction. This was followed by displacement of the chloro group with morpholine (neat) in quantitative yield, isolated as a crystalline solid on dilution of the reaction with methanol. Reduction of the nitro group with ammonium formate under an argon or nitrogen atmosphere provided 3-fluoro-4-morpholinoaniline as a crystalline solid which was converted to the isocyanate and treated with the chiral epoxide (S) N-(oxiranylmethyl)acetamide in xylene with lithium bromide and tributylphosphine oxide to yield linezolid. Alternatively, the intermediate 3-fluoro-4-morpholinoaniline was converted to the benzylcarbamate with benzyl chloroformate in aq. sodium bicarbonate, and subsequently treated with n-butyl lithium to form the anion and treated with (S) N-oxiranylmethyl)acetamide to provide linezolid.

Example 3

3-Fluoro-4-morpholinonitrobenzene (2). In a 250 ml 3-neck round bottom flask with mechanical stirrer, septum and drying tube was added 3,4-difluoronitrobenzene (1) (12.91 g, 81.1 mmol), methanol (60 ml) and morpholine (15.93 g, 16 ml, 183 mmol). The clear solution was heated at reflux with stirring for 2 hours. The reaction mixture containing yellow crystals was cooled in an ice bath for 1 hour with stirring. The crystals were collected by filtration and dried in vacuo (1 mm) at room temperature for 3 hours (16.99 g, 93%). Homogenous by TLC (silica gel, CHCL$_3$) Rf=0.54 (yellow spot) $^1$H NMR (500 MHz, CDCL3) δ 8.00 (ddd, 1H, J=9 Hz, J=2.6 Hz, J=1 Hz), 7.92 (dd, 1H, J=13.1 Hz, J=2.5 Hz), 6.92 (dd, 1H, J=8.8 Hz, J=8.8 Hz), 3.86 (dd, 4H, J=4.7 Hz, J=4.7 Hz), 3.28 (dd, 4H, J=4.7 Hz, J=4.7 Hz). LCMS (Method A) 0.79 min m/e 227.

Example 4

3-Fluoro-4-morpholinoaniline (5). 3-Fluoro-4-morpholinonitrobenzene (2) (16.99 gm, 75.11 mmol) and ammonium formate (19.5 gm, 309 mmol) were added to a 3-neck 500 ml round bottom flask with football stirrer. Methanol (185 ml) and reagent grade THF (45 ml) were added to the flask. The mixture was cooled in an ice bath and the flask was alternately evacuated (House vac) and filled with argon (4×) (Firestone valve). 10% Pd/C (450 mgs) was added and the reaction was evacuated (House vac) and filled with argon (2×) and was stirred in an ice bath over night allowing the reaction to warm to room temperature. The water-white reaction (when stirring stopped and catalyst allowed to settle) was treated with solid sodium ascorbate (4 gm) and diluted with ether (200 ml). Decanted the reaction solution from the dark solid (catalyst and salts) into a 1 L separatory funnel. Washed/decanted the dark solid with additional ether (50 ml) that was added to the separatory funnel. Brine (220 mL, containing 4 gm sodium ascorbate) was added to the separatory funnel and the organic layer separated. The aqueous layer was extracted with additional ether (100 ml). The combined ether layers were washed with brine (2×100 ml) (to remove MeOH—and water), dried (MgSO$_4$), diluted with benzene (25 ml) and evaporated providing a light yellow or a slightly reddish pink crystalline solid (13.3 gm, 90%). TLC (silica gel, EtOAc:Hexane 9:1) showed a single spot with lower $R_f$ than 2 that turned brown on standing in the air. Material used immediately in the next step (should be stored under argon or nitrogen until used).

Example 5

3-Fluoro-4-morpholinoaniline (5). Alternative procedure. 3-Fluoro-4-morpholinonitrobenzene (2) (12.6 gm, 55.67 mmol) and ammonium formate (14.45 gm, 229 mmol) was added to a 3-neck 500 ml rd bottom flask with football stirrer. Methanol (135 ml) and reagent grade THF (35 ml) were added to the flask. The mixture was warmed to obtain a homogenous solution and ammonium formate (14.45 gm, 229 mmol) was added forming a homogenous solution. The reaction was cooled in an ice bath and the flask was alternately evacuated (House vac) and filled with argon (4×) (Firestone valve). 10% Pd/C (335 mgs) was added and the reaction was evacuated (House vac) and filled with argon (2×) and was stirred in an ice bath overnight allowing the reaction to warm to room temperature. The water-white reaction (when stirring stopped and catalyst allowed to settle) was treated with solid sodium ascorbate (3 gm) and diluted with methylene chloride (150 ml). The reaction was decanted from the dark solid (catalyst and salts) into a 1 L separatory funnel. The dark solid was washed/decanted with additional methylene chloride (75 ml) that was added to the separatory funnel. Brine (175 ml, containing 2 gm sodium ascorbate) was added to the separatory funnel and the organic layer separated. The aqueous layer was extracted with additional methylene chloride (75 ml). The combined organic layers were washed with brine (2×75 ml containing 1 gm sodium ascorbate) (to remove MeOH—and water), dried (MgSO4), and evaporated providing a yellow orange crystalline solid (10 gm, 92%). TLC (silica gel, CHCl$_3$) $R_f$=0.18 (spot turns brown on exposure to UV light). Material used immediately in the next step (should be stored under argon or nitrogen until used).

Example 6

3-Fluoro-4-morpholinoisocyanate (6). 20% Phosgene in toluene (71 ml, 135 mmol) was cannulated into a dry 1 L 3-neck round bottom flask under argon that was fitted with a septum, overhead stirrer, and gas inlet tube. The septum was replaced with a 500 mL side arm dropping funnel that had an Argon inlet tube on top, and the gas inlet tube on the 1 L flask was replaced with a thermometer. The reaction was cooled in a dry ice acetone bath to ca. −20° C. with stirring. Aniline (5) (13.3 g, 67.8 mmol) was dissolved in warm (ca. 45° C.) toluene and added to the dropping funnel. The aniline solution was added to the rapidly stirring 20% phosgene solution in a slow stream keeping the reaction temperature at ~−20° C. Soon a thick milky white precipitate formed. After complete addition of the aniline, the dropping funnel was rinsed with toluene (25 ml). The dropping funnel was replaced with a reflux condenser with an argon inlet tube and the thermometer was replaced with a glass stopper. The milky white suspension was heated to reflux. After 30 to 40 minutes a homogeneous light colored solution formed. The reaction was refluxed an additional 15 minutes, cooled to room temperature and filtered through fluted filter paper to remove a small quantity of flocculent material, rinsing with toluene (15 ml). TLC of the light yellow filtrate (small aliquot diluted with MeOH, to make the methyl carbamate) showed a single spot. The filtrate was evaporated in vacuo to an almost colorless oil. The oil was poured into a 250 Erlenmeyer flask washing with hexane (total volume 60 ml). Within minutes off-white to light purple crystals formed. The crystalline mixture was cooled in an ice bath under argon and was collected by filtration (12.6 g, 84%) after drying in vacuo. LCMS (CH$_3$CN/MeOH as solvent to dissolve the crystals). Retention time 9.76 min (99%) m/e 255 (methyl carbamate M+).

Example 7

3-Fluoro-4-morpholinoisocyanate (6). Alternative procedure. 20% Phosgene in toluene (53 ml, 101 mmol) was cannulated into a dry 1 L 3-neck rd bottom flask under argon that was fitted with a septum, overhead stirrer, and gas inlet tube. The septum was replaced with a 500 ml side arm dropping funnel that had an Argon inlet tube on top, and the gas inlet tube on the 1 L flask was replaced with a thermometer. The reaction was cooled in a dry ice acetone bath to ca. −20° C. with stirring. Aniline (5) (10 g, 51 mmol) was dissolved in warm (ca. 45° C.) toluene (275 ml) and added to the dropping funnel. The aniline solution was added to the rapidly stirring 20% phosgene solution in a slow stream keeping the reaction temperature at ~−20° C. Soon a thick milky white precipitate formed. After complete addition of the aniline, the dropping funnel was rinsed with toluene (25 ml). The dropping funnel was replaced with a reflux condenser with an argon inlet tube and the thermometer was replaced with a glass stopper. The milky white suspension was heated to reflux. After 30 to 40 minutes a homogeneous light colored solution formed. The reaction was refluxed an additional 15 minutes, cooled to room temperature. TLC of the light yellow reaction (Small aliquot diluted with MeOH, to make the methyl carbamate) showed a single spot). The clear solution was evaporated in vacuo to a light colored oil. The oil was diluted with hexane (40 ml) and cooled in an ice bath. Within minutes white crystals formed and the mixture was cooled on dry ice for 15 minutes. The solvent was decanted from the crystals and the crystals were dried on the rotary evaporator (9.5 g, 84%). Used immediately for the preparation of (17). LCMS (Method A) (CH$_3$CN/MeOH as solvent to dissolve the crystals) Retention time 9.76 min (99%) m/e 255 (methyl carbamate M$^+$).

Example 8

(S)-(E,Z)-5-((Benzylideneamino)methyl)-3-(3-fluoro-4-morpholinophenyl)oxazolidin-2-one (13). Anhydrous LiBr (60 mg, 0.69 mmol), a 0.1 M solution of tri-n-butylphosphine oxide in o-xylene (6.4 ml, 0.64 mmol) and o-xylene (25 ml) were added to a 100 ml 1-neck rd bottom flask with football stirring bar. The mixture was refluxed for 50 minutes to dissolve the LiBr by azetropically removing water by distilling off ca. 12 ml of the xylene. A solution of 3-fluoro-4-morpholinoisocyanate (6) (2.39 g, 10.74 mmol) and (S) (E,Z)-N-benzylidene-1-(oxiran-2-yl)methanamine (10) (1.73 g, 10.74 mmol) in o-xylene (15 ml) was added to the reaction via a syringe in a slow stream. As the solution of (6) and (10) was added to the reaction the color rapidly lightened. The yellow-brown reaction solution was heated at reflux for 1 hr and during this time the color lightened. The reaction solution was cooled to room temp and added dropwise to a rapidly stirring solution of hexane (200 ml). A fine light tan precipitate formed that was collected by filtration and air dried (4.0 g, 97%). Recrystallizes nicely from ethanol. $^1$HNMR (CDCl$_3$) δ 8.39 (s, 1H), 7.70 (d, 2H, J=4.90 Hz), 7.38-7.46 (m, 4H), 7.14 (ddd, 1H, J=8.9 Hz, J=2.5 Hz, J=1.0 Hz), 6.92 (dd, 1H, J=9.2 Hz, J=9.2 Hz), 4.95 (m, 1H), 4.12 (dd, 1H, J=8.8 Hz, J=8.6 Hz), 4.07 (dd, 1H, J=8.7 Hz, J=6.1 Hz), 3.99 (ddd, 1H, J=12.7 Hz, J=4.6 Hz, J=1.3 Hz), 3.91 (ddd, 1H, J=13.2 Hz, J=5.6 Hz, J=1.0 Hz), 3.87 (dd, 4H, J=4.8 Hz, J=4.7 Hz), 3.05 (dd, 4H, J=4.6 Hz, J=4.6 Hz).

Example 9

(S)-N-[{3-[3-Fluoro-4-(morpholinyl)phenyl]-oxo-5-oxazolidyl]methylamine (11). Anhydrous LiBr (30 mg, 0.3 mmol) and tri-n-butylphosphine oxide (75 mg. 0.3 mmol) were added to a 25 ml 3-neck round bottom flask with football stirring bar containing o-xylene (10 ml). The mixture was refluxed for 50 minutes in an oil bath to azeotropically remove water. A solution of 3-fluoro-4-morpholinoisocyanate (6) and (S)(E,Z)-N-benzylidene-1-(oxiran-2-yl)methanamine (10) (720 mg, 4.47 mmol) in o-xylene (5 ml) was added to the reaction via a syringe in a slow stream. The light yellow-brown slightly cloudy reaction mixture was heated at reflux for 1 hr, cooled to room temp and poured into a rapidly stirring solution of hexane (75 ml). A fine precipitate formed that turned into semisolid. The mixture was stirred for 30 min and placed in the freezer overnight. The hexane was decanted from the precipitate; a mixture of white powder and light tan material. The precipitate was air dried. LCMS 5.27 min (40%) m/e 296, 6.17 min (38%) m/e 296 (apparently the same material since on further work-up only the 5.27 min peak observed), 7.85 min (8.5%) m/e 518, 9.77 min (6.7%) m/e 219 (Bu$_3$P=O). The solid was dissolved in 1 N HCl (50 ml) at room temp and rapidly stirred for 15 min to hydrolyze the remaining quantity of Shiff Base to (11) (most had already been converted to (11)). The solution was cooled with ice and extracted with EtOAc (50 ml). The aqueous layer was basified with ice cold 1 N NaOH (to ca. pH 8 to 9) and extracted with EtOAc (5×50 ml). The combined organic layers were washed with brine (25 ml), dried (MgSO$_4$/Na$_2$SO$_4$) and evaporated to a light purple semisolid (1.16 g, LCMS RT=5.07 min (79%) m/e 296, 6.23 min (8.3%), 219 (Bu3P=O). The solid was dissolved in CH$_2$Cl$_2$ (ca. 4 ml) and applied to a flash silica gel column (50 ml) packed with CH$_2$Cl$_2$. Elution with CH$_2$Cl$_2$ (200 ml) and then CH$_2$Cl$_2$:MeOH (9:1). When UV active material started to elute from the column, fractions were collected. The first two fractions contained material with an R$_f$~0.5 then a slow moving spot R$_f$~0.2 started to elute. Fractions containing the slow moving material (ca. 400 ml) were combined and evaporated to a white crystalline solid (710 mg, 54%) of 11. LCMS RT=5.38 min (100%) m/e=296 (MH$^+$). The faster eluting material was Bu$_3$P=O. LCMS RT=7.89 min m/e 219.

Example 10

(S)-N-[{3-[3-Fluoro-4-(morpholinyl)phenyl]-oxo-5-oxazolidyl]methylamine (11) hydrochloride. To a 50 ml 3-neck rd bottom flask with stirring bar and drying tube was added (S)-,E,Z)-5-((benzylideneamino)methyl)-3-(3-fluoro-4-morpholinophenyl)oxazolidin-2-one (13) (766 mg, 2 mmol) and EtOAc (8 ml). The mixture was heated to reflux to form a clear solution. The reaction solution was placed in a 45° C. oil bath with stirring and a solution of 1 N HCl in ethanol (10 ml, 10 mmol) (prepared by the addition of acetyl chloride to ethanol) was added dropwise. A white precipitate formed that went back in solution on complete addition of the ethanolic HCl leaving a cloudy white reaction mixture. (Dropwise addition prevents clumping of the precipitate). The reaction was stirred at 45° C. for 5 hours to overnight. The reaction was removed from the oil bath and ethyl acetate (15 ml) was added to the white crystalline solid. The solvent was separated from the crystals using a filter stick and a positive argon pressure. The crystals were washed with ethyl acetate (2×15 ml) and dried under vacuum using a Firestone valve. The white crystals were treated with refluxing ethanol (8 ml) and the resulting solution was gravity filtered through fluted filter paper into an Erlenmeyer flask and slowly cooled to room temp and then in an ice bath with stirring. The resulting off-white crystals of (11) hydrochloride (430 mg, 65%) were collected by filtration, washed with EtOH and dried in a vac oven (House vacuum) at 40° C. $^1$HNMR (DMSO-d6) δ 8.28 (s, 3H), 7.49 □ □ (dd, 1H, J=15 Hz, J=2.5 Hz), 7.18 (dd, 1H, J=8.8 Hz, J=2.2 Hz), 7.09 (dd, 1H, J=9.1 Hz, J=9.1 Hz), 4.92 (m, 1H), 4.16 (dd, 1H, J=9.1 Hz, J=9.1 Hz), 3.83 (dd, 1H, J=9.2 Hz, J=6.6 Hz), 3.74 (dd, 4H, J=4.5 Hz, J=4.5 Hz), 3.23 (t, 2H, J=5.4 Hz), 2.97 (dd, 4H, J=4.7 Hz, J=4.7 Hz). $^1$HNMR of the free amine (CDCl$_3$) δ 7.46 (dd, 1H, J=14.4 Hz, J=2.6 Hz), 7.14 (ddd, 1H, J=8.8 Hz, J=2.5 Hz, J=1.1 Hz), 6.93 (dd, 1H, J=9.2 Hz, J=9.1 Hz), 4.67 (m, 1H), 4.01 (dd, 1H, J=8.7 Hz, J=8.7 Hz), 3.88 (dd, 4H, J=4.8 Hz, J=4.6 Hz), 3.82 (dd, 1H, J=8.5 Hz, J=6.7 Hz), 3.11 (dd, 1H, J=13.7 Hz, J=4.1 Hz), 3.05 (dd, 4H, J=4.7 Hz, J=4.6 Hz), 2.97 (dd, 1H, J=13.7 Hz, J=5.7 Hz).

Example 11

(S)-N-[{3-[3-Fluoro-4-(morpholinyl)phenyl]-oxo-5-oxazolidyl]methyl]acetamide: Linezolid (9). In a dry 2-neck 15 ml round bottom flask with stirring bar, septum and reflux condenser containing an argon bubbler on top was added (S)—N-[{3-[3-fluoro-4-(morpholinyl)phenyl]-oxo-5-oxazolidyl]methyl]amine (11) (540 mg, 1.83 mmol) and CH$_2$Cl$_2$ (5 ml). Pyridine (320 mg, 0.33 ml, 4 mmol) and acetic anhydride (470 mg, 0.44 ml, 4.6 mmol) were added sequentially via syringe. The colorless reaction solution was heated at reflux under an argon atmosphere. The reaction was followed by LCMS and after 2 hrs was complete (small aliquot of reaction solution removed via syringe, diluted 4-fold with CH$_3$CN, filtered through a cotton plug in a pipette to remove cloudiness). LCMS shows RT 5.58 min m/e 338 (MH$^+$), 360 (M+23). The reaction was cooled to RT, poured into ice cold saturated aq. NaHCO$_3$ and diluted with additional CH$_2$Cl$_2$. Combined organic layers washed with brine (25 ml), ice cold 0.1 N aq HCl (25 ml), brine (2×25 ml) and dried (MgSO$_4$, Na$_2$SO$_4$) (the drying agent retained all the light purple color). The colorless filtrate was evaporated in vacuo to a white crystalline solid (150 mg, 24%) TLC (CH$_2$Cl$_2$:MeOH 9:1) R$_f$=0.4 identical with authentic linezolid (9). Recrystallized from EtOAc (2.5 ml) cooling to RT yielding white crystals cooled in freezer overnight (55 mg).

(S)(E,Z)-1-(Benzylideneamino)-3-chloropropan-2-ol (12). Benzaldehyde (5.95 g, 56 mmol), ethanol (25 ml) and conc. NH$_4$OH (5 g, 85 mmol) were added to a 100 ml round bottom flask with football stirring bar (resulting in a mild exotherm). (S)-Epichlorohydrin (5 g, 4.25 ml, 54 mmol) was added and the colorless reaction solution was heated at 40° C. (bath temperature) for 6 hr with stirring and allowed to stand at room temperature overnight. The reaction solution was evaporated to a colorless thick oil and diluted with water (5 ml). The solution was cooled on Dry Ice and then allowed to warm to room temperature forming white crystals (seeding-but not necessary). Decanted the water from the fine crystals (difficult to filter) and removed the rest of the water by warming the round bottom containing the crystals at 40° C. under high vacuum. (Crystals partially melted during the 30 min—cooled in an ice bath while continuing to pull vacuum at the the end of the 30 min). The white crystals were recrystallized from 300 ml of hot hexane removing a small amount of insoluble material by treating with Celite followed by gravity filtration through fluted filter paper—concentrated via reflux to 100 ml, cooled to room temperature and then in an ice bath. The resulting white crystals were collected by filtration and dried at room temperature (House vacuum) (7.53 g, 70.6%), GCMS retention time 8.84 min, m/e 196.

Example 12

(S)(E,Z)-N-benzylidene-1-(oxiran-2-yl)methanamine (10). (S)(E,Z)-1-(Benzylideneamino)-3-chloropropan-2-ol (12) (2.55 g, 12.9 mmol), reagent grade methanol (65 ml) and anhydrous $K_2CO_3$ (3.56 g, 25.8 mmol) were added to a 250 ml round bottom flask with football stirrer and drying tube. The reaction mixture was stirred vigorously (rate of stirring determines rate of heterogeneous reaction). After 2 hrs GCMS showed complete conversion to the epoxide (small aliquot removed from the reaction, diluted with an equal volume of $CH_3CN$, filtered through pipette with a cotton plug in a disposable pipette). Retention time 7.77 min, m/e 160 (the methoxyalcohol from opening the epoxide has retention time 8.67 min m/e 192) (substantial formation of this material observed if reaction allowed to proceed overnight). The colorless reaction was diluted with $CH_2Cl_2$ (100 ml) and the aqueous layer was extracted with additional $CH_2Cl_2$ (2×50 ml). The combined organic layers were washed with brine (3×100 ml), dried ($MgSO_4/Na_2SO_4$) and evaporated to a colorless oil (2.1 g, quantitative yield); $^1H$ NMR (500 MHz, $CDCl_3$) δ 8.29 (s, 1H), 7.73-7.75 (m, 2H), 7.40-7.43 (m, 3H), 3.90-3.93 (m, 1H), 3.68-3.72 (m, 1H), 3.32-3.35 (m, 1H), 2.84-2.87 (m, 1H), 2.73-2.75 (m, 1H); MS (EI, 70 eV) m/z 161 ($M^+$, 3), 160 (17), 144 (23), 132 (39), 118 (43), 104 (53), 91 (100). GCMS shows essentially pure epoxide; used directly to prepare 11. GCMS Retention time 7.76 min (m/e 160).

Example 13

3-Fluoro-4-morpholinobenzoic acid (14). A 500 ml 3-neck rd bottom flask fitted with mechanical stirrer was charged with 3,4-difluorobenzoic (15.8 g, 100 mmol) and morpholine (70 g, 70 ml, 800 mmol). The clear solution was heated at reflux with stirring for 30 hours. The heating source was removed from the reaction mixture that contained a few crystals on the side of the flask and was acidified (pH 1 to pH 2) with 6 N hydrochloric acid with rapid stirring. The product started to precipitate as the pH drops below 6. The precipitate was collected by filtration and washed thoroughly with warm (50° C.) water (500 ml) and dried at 110° C. under house vacuum. The product was recrystallized by dissolving in refluxing ethanol (500 ml) and concentrated to 200 ml with stirring. Crystals stated to form in the refluxing solution when the volume had been reduced to ca. 400 ml. The crystals were cooled to room temp with stirring, cooled in an ice bath for 1 hour with stirring, collected by filtration and dried in vacuo (House vac at 80° C.) (17.1 g, 76%). $^1H$ NMR (500 MHz, DMSO-$d_6$) δ 7.69 (d, 1H, J=8.4 Hz), 7.58 (dd, 1H, J=13.9 Hz, J=1. Hz), 7.09 (dd, 1H, J=8.6 Hz, J=8.6 Hz), 3.75 (dd, 4H, J=4.5 Hz, J=4.5 Hz), 3.12 (dd, 4H, J=4.5 Hz, J=4.5 Hz).

Example 14

3-Fluoro-4-morpholinobenzoic acid (14). Alternative method. This compound was alternatively prepared following the literature procedure of Fujisaki et al. (*Heterocycles* 2008, 75, 1681-1694), using DMSO as solvent. However, a lower yield is obtained with this method.

Example 15

3-Fluoro-4-morpholinobenzoic acid (14). Alternative method. A 15 ml ACE Glass crew cap thick walled vessel with magnetic stirring bar was charged with morpholine (5 ml, 28.5 mmol), sulfolane (5 ml) and 3,4-difluorobenzoic acid (1.12 g, 7.1 mmol). The vessel was sealed with the screw cap and heated with stirring at 170 to 175° C. (oil bath temperature) for 3 hours. The vessel was cooled in an ice bath. NMR (DMSO-$d_6$) of the precipitate formed from a small aliquot of the acidified reaction indicated complete conversion to (14). The reaction was diluted with an equal volume of water and acidified to ca. pH 2 to 3 with 6 N hydrochloric acid. The resulting white precipitate was collected by filtration and washed with refluxing water (50 ml) to ensure the removal of morpholine hydrochloride (that appear as two triplets just above the morpholine peaks for (14) in the NMR). The white precipitate was dried at 110° C. under house vacuum (1.35 g, 81% and recrystallized from methanol (1.0 g, 62.5%). $^1H$ NMR (500 MHz, DMSO-d6) δ 7.69 (d, 1H, J=8.4 Hz), 7.58 (dd, 1H, J=13.9 Hz, J=1. Hz), 7.09 (dd, 1H, J=8.6 Hz, J=8.6 Hz), 3.75 (dd, 4H, J=4.5 Hz, J=4.5 Hz), 3.12 (dd, 4H, J=4.5 Hz, J=4.5 Hz).

Example 16

Scale-up of the synthesis of 3-fluoro-4-morpholinobenzoic acid (14). A 2 L 3-neck round bottom flask fitted with mechanical stirrer and reflux condenser was charged with morpholine (700 g, 700 ml, 8 mol) and to the stirring solution was added 3,4-difluorobenzoic acid (158 g, 1 mol) (AmplaChem, Inc). The clear solution was heated at reflux and after 29 hours a ca. 0.5 ml aliquot was removed from the light yellow reaction solution, acidified with 6 N HCl and the precipitate was analyzed by $^1H$ NMR (DMSO-$d_6$) showing that the reaction was complete by the absence of the aromatic peaks at δ7.78-7.92 present in the starting material. The reaction was allowed to cool to below 100° C. and was carefully acidified (pH 1 to 2) with 6 N hydrochloric acid with rapid stirring (initial addition of 6N HCl was dropwise but then as a slow stream with cooling). The product starts to precipitate as the pH falls below 6. The precipitate was collected by filtration and washed thoroughly with hot (80° C.) water (2 L) to ensure the removal of morpholine hydrochloride (that appears as two triplets just above the morpholine peaks for (14) in the NMR) The white precipitate was dried at 110° C. under house vacuum and recrystallized by dissolving in ethanol (4.5 L) and concentration to 1.5 L with stirring. Crystals started to form in the refluxing solution when the volume had been reduced to ca. 3.5 L. The crystals were cooled to room temp with stirring, cooled in an ice bath for 1 hour with stirring, collected by filtration and dried in vacuo at 80° C. (172.5 g, 77%). $^1H$ NMR spectrum identical with that for the product described in the previous paragraph.

Example 17

3-Fluoro-4-morpholinobenzoyl azide (15). Thionyl chloride method. 3-Fluoro-4-morpholinobenzoic acid (14) (16.2 gm, 72 mmol) and methylene chloride (180 ml) were added to a 500 ml rd bottom flask with football stirrer and reflux condenser. Thionyl chloride (15.8 ml, 216 mmol) and dry DMF (0.7 ml) were added to the flask. The mixture was heated at a gentle reflux and within a few minutes a light yellow solution formed and gas evolution subsided. The reaction was heated at reflux for 45 minutes. TLC ($CH_2Cl_2$: MeOH; 95:5) of a small aliquot of the reaction that was quenched in methanol (to form the methyl ester) indicated complete conversion to the acid chloride. The light yellow solution was evaporated to dryness in vacuo providing a light yellow solid. Hexane (75 ml) was added and the flask was swirled for a few minutes. The hexane was evaporated in vacuo yielding crystalline mass. Hexane (75 ml) was added to the crystals, the flask was swirled and the light yellow solution was decanted from the white crystalline mass of the acid chloride. The solid was dissolved in acetone (200 ml) at room temp and the solution was cooled in an ice bath with stirring. A solution of sodium azide (27 g, 415 mmol) in water (100 ml) was added as a slow stream to the rapidly stirring reaction solution. A white granular precipitate formed in the reaction mixture by the time all of the sodium azide solution had been added. The ice bath was removed and replaced with a room temp water bath. After 45 minutes the granular precipitate had dissolved and the two phase reaction solution was rapidly stirred an additional 45 minutes. The reaction was diluted with methylene chloride (150 ml) and the lower colorless organic layer was separated from the upper light orange aqueous layer. The aqueous layer was extracted with additional methylene chloride (75 ml) and the combined organic layers were washed with ice cold 10% aq. sodium carbonate, water (100 ml) and dried over sodium sulfate overnight. The drying agent was removed by filtration and the colorless solution was evaporated to dryness in vacuo (bath temp 35° C.) forming a white crystalline solid. Hexane (75 ml) was added and the crystalline mass was stored a −20° C., collected by filtration (without washing with hexane) and air dried (15.55 g, 86%) TLC (silica gel $CH_2Cl_2$) showed a single spot that turned brown on exposure to UV light. mp 86.1-86.6° C. (without decomp); IR (thin film) 2154, 1675 cm$^{-1}$; $^{13}$C NMR (125 MHz, CDCl$_3$) δ 170.91, 154.09, 145.07, 126.72, 123.66, 117.42, 117.31, 66.70, 49.97.

Example 18

3-Fluoro-4-morpholinobenzoyl azide (15). Phosphorus pentachloride method. 3-Fluoro-4-morpholinobenzoic acid (14) (2.25 gm, 10 mmol), methylene chloride (25 ml) and phosphorus pentachloride (2.19 gm, 10.5 mmol) were added to a 100 ml round bottom flask with football stirrer and reflux condenser. The reflux condenser was fitted with a T-tube on top that had a line connected to a nitrogen tank for a slight positive nitrogen inflow and a line connected to a drying tube that led to a gas scrubber to trap hydrogen chloride gas. The mixture was heated at a gentle reflux for 90 minutes with stirring. At this time the reaction was a homogenous light yellow solution. TLC ($CH_2Cl_2$:MeOH; 95:5) of a small aliquot of the reaction that was quenched in methanol (to form the methyl ester) indicated complete conversion to the acid chloride. The mixture was evaporated to dryness in vacuo providing a light yellow solid. Hexane (25 ml) was added and the flask was swirled for a few minutes. The hexane was evaporated in vacuo yielding a crystalline mass. Hexane (25 ml) was added to the crystals, the flask was swirled and the solution was decanted from the light yellow crystals. The small amount of hexane remaining with the crystals was removed in vacuo. The acid chloride was dissolved in acetone (18 ml) at room temperature and a solution of sodium azide (3.25 gm, 50 mmol) in water (12 ml) was added to the rapidly stirring solution. The two phase solution remained at room temperature and was vigorously stirred. After ca. 10 minutes light yellow crystals formed in the reaction flask. Additional acetone (10 ml) was added to the reaction to dissolve the crystals. After one hour the two phase solution was transferred to a separatory funnel. TLC (CHCL$_3$) of the two layers showed that most of the benzoyl chloride was in the upper layer. The lower layer was extracted with methylene chloride (25 ml) and the lower layer was discarded. The methylene chloride extract was added to the upper layer plus an additional 25 ml of methylene chloride. The light lemon yellow solution was extracted with ice cold 10% aq. sodium carbonate (2×10 ml), water (25 ml) and dried (Na$_2$SO$_4$) over night. The drying agent was removed by filtration and the lemon yellow solution was evaporated to dryness in vacuo (bath temp 35° C.) to a light yellow crystalline solid. Cold hexane (−15° C.) (15 ml) was added and the light yellow crystals were collected by filtration and air dried (2.3 g, 92%); TLC R$_f$=0.15 (silica gel, CHCL$_3$) (spot turns brown on exposure to UV light); mp 85.0-85.9° C. (without decomp); IR (thin film) 2154, 1675 cm-1; $^1$H NMR (500 MHz, DMSO-d6) δ 7.76 (dd, 1H, J=9.0 Hz, J=2.0 Hz), 7.67 (dd, 1H, J=13.8 Hz, J=2.0 Hz), 6.94 (dd, 1H, J=8.5 Hz, J=8.5 Hz), 3.88 (dd, 4H, J=4.6 Hz, J=4.6 Hz), 3.5 (dd, 4H, J=4.7 Hz, J=4.7 Hz). $^{13}$C NMR (125 MHz, CDCL3) δ 170.88, 155.11, 144.78, 126.73, 123.90, 117.60, 117.38, 65.82, 50.04.

Example 19

3-Fluoro-4-morpholinobenzoyl azide (15). Alternative method. This compound may be prepared from (14) in a one pot reaction utilizing POCl$_3$ in DMF (Vilsmeier complex) and NaN$_3$ following the literature procedure of Sridhar et al. (*Syn. Comm.* 2003, 33, 607-611).

Example 20

(S)-(E,Z)-5-((4-Chlorobenzylideneamino)methyl)-3-(3-fluoro-4-morpholinophenyl)oxazolidin-2-one (17). Anhydrous LiBr (168 mg, 1.9 mmol), a 0.1 M solution of tri-n-butylphosphine oxide in o-xylene (19 ml, 1.9 mmol) and o-xylene (100 ml) were added to a 250 ml 3-neck rd bottom flask with football stirring bar, reflux condenser that was fitted with an argon inlet valve and a 125 ml sidearm dropping funnel. The mixture was refluxed for 30 minutes to dissolve the LiBr by azetropically removing water by distilling off ca. 10 ml of the xylene. A solution of 3-fluoro-4-morpholinobenzoyl azide (15) (6.25 g, 25 mmol) and (S)(E,Z)-N-(4-chlorobenzylidene)-1-(oxiran-2-yl)methanamine (16) (5.0 g, 25.6 mmol) in o-xylene (50 ml) was placed in the dropping funnel and added dropwise to the refluxing reaction with stirring. As the solution of (15) and (16) was added the reaction solution turned yellow. The reaction was heated at reflux for 30 minutes, removed from the heat source and gravity filtered through fluted filter paper into a dropping funnel to remove a small quantity of insoluble material. The warm solution was added dropwise to a rapidly stirring solution of hexane (500 ml). A fine light yellow precipitate formed that was collected by filtration and air dried (7.1 g, 68%). Recrystallization of the yellow solid from 50 ml of toluene (filtered to remove small quantity of insoluble material) (seeded), cooling and storing the crystals overnight at −20° C. gave white crystals that were collected by filtration and washed with cold toluene (6.75 g, 65%) after drying in vacuo at 40° C. $^1$H NMR (500 MHz, DMSO-d$_6$) δ 8.39 (s, 1H), 7.70 (d, 2H, J=4.90 Hz), 7.38-7.46 (m, 4H), 7.14 (ddd, 1H, J=8.9 Hz, J=2.5 Hz, J=1.0 Hz), 6.92 (dd, 1H, J=9.2 Hz, J=9.2 Hz), 4.95 (m, 1H), 4.12 (dd, 1H, J=8.8 Hz, J=8.6 Hz), 4.07 (dd, 1H, J=8.7 Hz, J=6.1 Hz), 3.99 (ddd, 1H, J=12.7 Hz, J=4.6 Hz, J=1.3 Hz), 3.91 (ddd, 1H, J=13.2 Hz, J=5.6 Hz, J=1.0 Hz), 3.87 (dd, 4H, J=4.8 Hz, J=4.7 Hz), 3.05 (dd, 4H, J=4.6 Hz, J=4.6 Hz).

Example 21

(S)-(E,Z)-5-((4-Chlorobenzylideneamino)methyl)-3-(3-fluoro-4-morpholinophenyl)oxazolidin-2-one (17). Alternative procedure from isolated isocyanate 6. Anhydrous LiBr (190 mg, 2.2 mmol) and tri-n-butylphosphine oxide (537 mg, 2.5 mmol) were quickly added to a 250 ml 3-neck round bottom flask containing toluene (110 ml) with football stirring bar. A 125 ml dropping funnel with side arm and reflux condenser that had an argon gas bubbler on top were placed on the flask and the mixture was refluxed for 30 minutes under argon allowing toluene to distill from the reaction flask, to azetropically remove water, resulting in a clear solution. A solution of 3-fluoro-4-morpholinoisocyanate (6) (9.5 g, 42.8.mmol) and (S)(E,Z)-N-4-chlorobenzylidene-1-(oxiran-2-yl)methanamine (16) (9.2 g, 47 mol) in toluene (45 ml) in the dropping funnel was added to the refluxing reaction in a slow stream over 15 minutes. The golden yellow reaction solution was heated at reflux an additional 45 minutes, cooled in an ice bath and seeded resulting in the formation of a copious amount of light yellow crystals. The reaction mixture was cooled to −15° C. overnight and the light yellow crystals were collected by filtration and washed with cold (−15° C.) toluene (2×15 ml) and dried in the vacuum oven at 50° C. (12.7 g, 71%). NMR was identical with spectrums from previous runs that were recrystallized from toluene.

Example 22

(S)-(E,Z)-5-((4-Chlorobenzylideneamino)methyl)-3-(3-fluoro-4-morpholinophenyl)oxazolidin-2-one (17). Alternative procedure from isolated isocyanate (6) using magnesium bromide etherate as catalyst instead of lithium bromide and tri-n-butylphosphine oxide. Magnesium bromide etherate (111 mg, 0.43 mmol) was added to a dry 25 ml 3-neck round bottom flask containing toluene (8 ml) with football stirring bar. A 10 ml addition funnel with side arm and reflux condenser that had an argon gas bubbler on top were placed on the flask and the mixture was heated to reflux under argon. A solution of 3-fluoro-4-morpholinoisocyanate (6) (0.95 g, 4.28 mmol) and (S)(E,Z)-N-4-chlorobenzylidene-1-(oxiran-2-yl)methanamine (16) (0.92 g, 4.7 mol) in toluene (8 ml) was added to the dropping funnel and the solution was added to the refluxing reaction in a slow stream over 5 minutes. The magnesium bromide etherate went into solution and the resulting golden yellow reaction was heated at reflux for 45 minutes, cooled in an ice bath and seeded, resulting in the formation of yellow crystals. The reaction mixture was cooled to −15° C. overnight and the yellow crystals were collected by filtration and washed with cold (−15° C.) toluene (2×15 ml) and air dried. Recrystallization from toluene (10 ml) (removing small amount of insoluble material by gravity filtration) provided 0.7 gm of yellow crystals (56%). The $^1$H NMR spectrum was identical with spectra of compound (17) from previous runs that were recrystallized from toluene, as described above.

Example 23

Scale-up of synthesis of (S)-(E,Z)-5-((4-chlorobenzylideneamino)methyl)-3-(3-fluoro-4-morpholinophenyl)oxazolidin-2-one (17). Anhydrous LiBr (ca. 2.4 g, 7.6 mmol), and tri-n-butylphosphine oxide (6.0 g, 38 mmol) were quickly added to a 2 L 3 neck round bottom flask containing o-xylene (500 ml) that was outfitted with a 500 ml side arm dropping funnel and reflux condenser with an argon gas inlet valve on top and a football stirring bar. The mixture was refluxed for 30 minutes with stirring to azetrope off any water and to dissolve the LiBr by distilling off ca. 50 ml of the xylene. A solution of 3-fluoro-4-morpholinobenzoyl azide (15) (90 g, 0.36 mol) and (S)(E,Z)-N-(4-chlorobenzylidene)-1-(oxiran-2-yl)methanamine (16) (72 g, 0.368 mol) in o-xylene (400 ml) dissolved by warming to 35° C. with stirring in a 1 L Erlenmeyer flask (adding the epoxide to the Erlenmeyer flask initially assists the dissolution of benzoyl azide (15)) was placed in the dropping funnel and added to the refluxing reaction with stirring over 1 hr. As the solution of (15) and (16) was added the reaction solution turned golden brown and gas evolution was observed. (Caution not to add too rapidly due to the gas evolution). The reaction was heated at reflux an additional 30 minutes, cooled in an ice bath with stirring providing yellow crystals from the golden yellow-brown reaction. The mixture was stored overnight at −15° C. and the light yellow crystals were collected by filtration and washed with cold (−20° C.) toluene (250 ml). Recrystallization of the air dried crystals (107 g) from 1 L of toluene (filtered the refluxing mixture after adding Celite to remove a small quantity of insoluble material) and refluxing down to a volume of 700 ml (allowing to cool to room temperature with stirring and then in an ice bath for 30 minutes) gave off white crystals that were collected by filtration and washed with cold toluene (89.2 g, 59.3%). after drying in vacuo at 40° C. $^1$H NMR spectrum identical with that for the product described in the previous paragraph.

Example 24

(S)-N-[{3-[3-Fluoro-4-(morpholinyl)phenyl]-oxo-5-oxazolidyl]methyl]acetamide: Linezolid (9). Alternate route from (S)-(E,Z)-5-((4-chlorobenzylideneamino)methyl)-3-(3-fluoro-4-morpholinophenyl)oxazolidin-2-one (17). To a 100 ml rd bottom flask with a football stirring bar was added (17) (2.09 g, 5 mmol), methylene chloride (15 ml) and water (15 ml) followed by 12 N hydrochloric acid (0.84 ml, 10 mmol). The mixture was rapidly stirred at room temp and within 15 minutes a two-phase clear solution formed. The reaction was stirred for 45 minutes and the lower organic layer was discarded. The aqueous layer was washed with additional methylene chloride (15 ml) and discarded. Methylene chloride (15 ml) was added to the aqueous layer and the two-phase solution was neutralized with 2 N sodium hydroxide (ca. 4.5 ml) to pH 7 while stirring the reaction in an ice bath. The ice bath was removed from the reaction flask and acetic anhydride (1.5 ml, 15 mmol) was added all at once to the rapidly stirring solution and the mixture was stirred at room temp for 10 minutes and was neutralized to pH 7 with 2 N sodium hydroxide (ca. 5 ml). The organic layer was separated and the aqueous layer was extracted with additional methylene chloride (2×15 ml). The combined organic layers were dried (MgSO$_4$) and evaporated in vacuo to a solid The solid was recrystallized from ethyl acetate (dissolved in 35 ml of refluxing EtOAc and refluxed to a volume of 20 ml). The crystals were allowed to cool to ambient temperature and after 30 minutes cooled in an ice bath. The white crystals of 9 were collected by filtration and dried in vacuo at room temp (1.1 g, 65%) homogenous by TLC (CH$_2$Cl$_2$:MeOH 9:1) and LCMS (Method B) 5.71 min m/e 338. $^1$H NMR (500 MHz, CDCl$_3$) δ 7.44 (dd, 1H, J=13.8 Hz, J=2.6 Hz), 7.08 (dd, 1H, J=8.8 Hz, J=2.6 Hz), 6.93 (t, 1H, J=9 Hz), 6.1 (bt, 1H, J=6.1 Hz), 4.8 (m, 1H), 4.0 (t, 1H. J=8.9 Hz), 3.87 (t, 4H, J=4.5 Hz), 3.75 (dd, 1H, J=9.1 Hz, 6.8 Hz), 3.70 (ddd, 1H, J=11.6 Hz, J=5.9 Hz, J=3.1 Hz), 3.62 (dt, 1H, J=14.7. J=6.0 Hz), 3.05 (t, 4H, J=4.5 Hz), 2.02 (s, 3H); [α]$^{25}_D$ –13.0° (c=1.00, EtOH). An additional 480 mg of 9 was isolated from the filtrate as a white crystalline solid.

Example 25

Scale-up of synthesis of (S)-N-[{3-[3-fluoro-4-(morpholinyl)phenyl]-oxo-5-oxazolidyl]methyl]acetamide: Linezolid (9). To a 2 L 3 neck round bottom flask with overhead stirrer was added water (425 ml), 12 N hydrochloric acid (34 ml, 408 mmol), methylene chloride (340 ml) and (S)-(E,Z)-5-((4-chlorobenzylideneamino)methyl)-3-(3-fluoro-4-morpholinophenyl)oxazolidin-2-one (17) (85 g, 203.4 mmol) rinsed in with methylene chloride (85 ml). The mixture was rapidly stirred at room temp and within 30 minutes a two-phase clear homogenous solution formed. The reaction was stirred for 1 hour and the orange yellow lower organic layer was discarded. The lemon yellow aqueous layer was washed with additional methylene chloride (200 ml) and the methylene chloride was discarded. Methylene chloride (425 ml) was added to the aqueous layer and the two phase solution was transferred to a 2 L Erlenmeyer flask, cooled in an ice bath and neutralized to ca. pH 7 with ice cold 6 N NaOH (ca. 45 ml) while stirring the reaction in the ice bath. The reaction changed in color from yellow to colorless and a white precipitate formed from the reaction flask and acetic anhydride (72 ml, 720 mmol) was added all at once to the rapidly stirring mixture. The mixture was vigorously stirred at room temp for 1 hour yielding a light yellow clear 2-layer solution. The solution was cooled in an ice bath and made basic (ca. pH 9) with 6 N sodium hydroxide. The lower organic layer was separated and the aqueous layer was extracted with additional methylene chloride (3×100 ml). The combined organic layers were dried (MgSO$_4$) and evaporated (bath temp 25° C.) to a volume of ca. 400 ml. The light yellow solution crystallized to a thick mass of white crystals that was diluted with refluxing ethyl acetate (250 ml) and the slurry was poured into a stirring refluxing solution of ethyl acetate (800 ml) (total volume 1600 ml) that was refluxed down to a volume of 1 L. An additional 500 ml of hot ethyl acetate was added and concentrated by refluxing to a volume of 1 L with stirring. TLC (CH$_2$Cl$_2$:MeOH 9:1) of the recrystallization mixture showed pure product. The flask was stirred at room temp overnight and cooled in an ice bath for 30 minutes before the white crystals of (9) were collected by filtration, air dried and dried in vacuo at 35° C. (57.7 g, 84%) homogenous by TLC (CH$_2$Cl$_2$:MeOH 9:1, R$_f$=0.54) and LCMS (Method B) 5.71 min m/e 338. $^1$H NMR spectrum identical with that for the product described in the previous paragraph; [α]$^{25}_D$ –13.6° (c=1.00, EtOH). Chiral chromatography: Retention time 12.97 min (100%)>98% ee) (m/e 338) chromatogram showed undetectable levels of the R enantiomer which has a Retention time of 14.44 min).

Example 26

Scale-up of synthesis of (S)-N-[{3-[3-fluoro-4-(morpholinyl)phenyl]-oxo-5-oxazolidyl]methyl]acetamide: Linezolid (9). Alternative procedure. To a 2 L 3 neck round bottom flask with overhead stirrer was added water (500 ml), 12 N hydrochloric acid (40 ml, 480 mmol), methylene chloride (400 ml) and (S)-(E,Z)-5-((4-chlorobenzylideneamino)methyl)-3-(3-fluoro-4-morpholinophenyl)oxazolidin-2-one (17) (100 g, 239 mmol) rinsed in with methylene chloride (100 ml) The mixture was rapidly stirred at room temp and within 30 minutes a two-phase clear homogenous solution formed. The reaction was stirred for 1 hour and the orange yellow lower organic layer was discarded. The lemon yellow aqueous layer was washed with additional methylene chloride (250 ml) and the methylene chloride was discarded. Methylene chloride (500 ml) was added to the aqueous layer and the two phase solution was transferred to a 2 L Erlenmeyer flask, cooled in an ice bath and neutralized to ca. pH 7 with ice cold 6 N NaOH (ca. 50 ml) while stirring the reaction in an ice bath. The reaction changed in color from yellow to colorless and a white precipitate formed that went back into solution with continued stirring. The ice bath was removed from the reaction flask and acetic anhydride (72 ml, 720 mmol) was added all at once to the rapidly stirring solution. The mixture was stirred at room temp for 15 minutes, cooled in an ice bath and made basic (ca. pH 9) with 6 N sodium hydroxide (ca. 350 ml). The lower organic layer was separated and the aqueous layer was extracted with additional methylene chloride (3×150 ml). The combined organic layers were dried (MgSO$_4$) and evaporated (bath temp 25° C.) to a volume of ca. 400 ml. The light yellow solution was slowly added to a stirring refluxing solution of ethyl acetate (800 ml) and refluxed down to a volume of 800 ml. Hot ethyl acetate was added to a volume of 1800 ml and the milky solution was treated with Celite (caution to avoid foaming) filtered and concentrated by refluxing to a volume of 1100 ml with stirring. Crystals started forming in the refluxing solution at a volume of ca. 1250 ml. The flask was stirred at room temp overnight and cooled in an ice bath for 30 minutes before the white crystals of (9) were collected by filtration, air dried and dried in vacuo at room temp (62.1 g, 77%) homogenous by TLC (CH$_2$Cl$_2$:MeOH 9:1, Rf=0.54) and LCMS (Method B) 5.71 min m/e 338. All analytical and spectral data for this compound were identical with those described previously herein.

Example 27

(S)(E,Z)-1-(4-Chlorobenzylideneamino)-3-chloropropan-2-ol (18). 4-Chlorobenzaldehyde (7.85 g, 56 mmol), ethanol (25 ml) and conc NH$_4$OH (5 g, 86 mmol) were added to a 100 ml rd bottom flask with football stirring bar. (S)-Epichlorohydrin (5 g, 4.25 ml, 54 mmol) (TCI America, Lot: AZR7B, min 98% purity) was added and the colorless reaction solution was heated at 40° C. (bath temp) for 6 hr with stirring and allowed to stand at room temp overnight. The reaction solution was diluted with methylene chloride (150 ml) and brine (125 ml). The organic layer was separated and the aqueous layer extracted with additional methylene chloride (50 ml). The combined organic layers were washed with brine (75 ml), dried (MgSO$_4$) and evaporated to dryness yielding a colorless oil that was crystallized from hexane (9.0 g, 72%). GCMS Retention time 10.03 min (m/e 232).

Example 28

(S)(E,Z)-1-(4-Chlorobenzylideneamino)-3-chloropropan-2-ol (18). Alternative procedure. 4-Chlorobenzaldehyde (15.7 gm 112 mmol), methanol (50 ml) and conc $NH_4OH$ (10 g, 172 mmol) were added to a 250 ml round bottom flask with football stirring bar. (S)-Epichlorohydrin (10 g, 8.5 ml, 108 mmol) (Atlantic SciTech Group, Inc) (98% purity) was added and the colorless reaction solution was heated at 40° C. (bath temp) for 6 hr with stirring and allowed to stand at room temp overnight. GCMS analysis of the reaction solution indicated complete reaction. The reaction solution was diluted with methylene chloride (100 ml) and brine (75 ml). The organic layer was separated and the aqueous layer extracted with additional methylene chloride (25 ml). The combined organic layer was washed with brine (50 ml), dried ($MgSO_4$) and evaporated to a white crystalline solid. (In previous runs initially isolated as an oil that was seeded). The crystals were treated with hexane (30 ml), cooled overnight at −15° C. and collected by filtration, air dried and then dried in a vacuum oven for 3 hours at room temp (19.5 g, 75%); $^1H$ NMR (500 MHz, DMSO-$d_6$) δ 8.34 (s, 1H), 7.78 (d, 2H, J=8.5 Hz)), 7.52 (d, 2H, J=8.5 Hz), 5.29 (d, 1H, J=5.4 Hz), 3.94 (dd, 1H, J=13 Hz, J=6.1 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 10.03 min (m/e 232).

Example 29

Scale-up of the synthesis of (S)(E,Z)-1-(4-chlorobenzylideneamino)-3-chloropropan-2-ol (18). 4-Chlorobenzaldehyde (157 g 1.12 mol), ethanol (500 ml) and conc $NH_4OH$ (100 g, 1.72 mol) were added to a 2 L round bottom flask with football stirring bar. (S)-Epichlorohydrin (100 g, 85 ml, 1.08 mol) (Atlantic SciTech Group, Inc) (98% purity) was added and the colorless reaction solution was heated at 40° C. (bath temp) for 6 hr with stirring and allowed to stand at room temp overnight. GCMS analysis of the reaction solution indicated complete reaction. The reaction solution was diluted with methylene chloride (1 L) and brine (700 ml). The organic layer was separated and the aqueous layer extracted with additional methylene chloride (250 ml). The combined organic layer was washed with brine (500 ml), dried ($MgSO_4$) and evaporated to a white crystalline solid. (Note: In previous smaller runs initially isolated as an oil that was seeded). The crystals were treated with hexane (200 ml), cooled in an ice bath and collected by filtration and washed with 50 ml of cold (−20° C.) hexane, air dried and then dried in a vacuum oven for 3 hours at room temp (165 g, 66%); $^1H$ NMR (500 MHz, DMSO-$d_6$) δ 8.34 (s, 1H), 7.78 (d, 2H, J=8.5 Hz), 7.52 (d, 2H, J=8.5 Hz), 5.29 (d, 1H, J=5.4 Hz), 3.94 (dd, 1H, J=13 Hz, J=6.1 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 10.03 min (m/e 232).

Example 30

(S)(E,Z)-N-4-Chlorobenzylidene-1-(oxiran-2-yl)methanamine (16). (S)(E,Z)-1-(4-Chlorobenzylideneamino)-3-chloropropan-2-ol (18) (8.9 g, 38.4 mmol), reagent grade methanol (250 ml) and anhydrous $K_2CO_3$ (10.5 g, 76.7 mmol) were added to a 500 ml rd bottom flask with football stirrer. The reaction mixture was stirred vigorously. After 2 hrs GCMS showed complete conversion to the epoxide (Small aliquot removed from the reaction, diluted with an equal volume of $CH_3CN$, filtered thru disposable pipette with a cotton plug) Retention time 8.95 min, m/e 194. The colorless reaction was diluted with $CH_2Cl_2$ (150 ml) and brine (100 ml). The aqueous layer was extracted with additional $CH_2Cl_2$ (75 ml). The combined organic layers were washed with brine (3×75 ml), dried ($MgSO_4$) and evaporated (bath temp 45° C.) to a colorless oil (6.9 g, 92%); $^1H$ NMR (500 MHz, DMSO-$d_6$) δ 8.35 (s, 1H), 7.78 (d, 2H, J=8.2 Hz)), 7.53 (d, 2H, J=8.2 Hz), 3.89 (ddd, 1H, J=13 Hz, J=3.5 Hz, J=1.6 Hz), 3.55 (ddd, 1H, J=13 Hz, J=6.1 Hz, J=1.3 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 8.95 min (m/e 194).

Example 31

Scale-up of synthesis of (S)(E,Z)-N-4-chlorobenzylidene-1-(oxiran-2-yl)methanamine (16). (S)(E,Z)-1-(4-Chlorobenzylideneamino)-3-chloropropan-2-ol (18) (163 g, 0.7 mol), reagent grade methanol (1.5 L) and anhydrous $K_2CO_3$ (193 g, 1.4 mol) were added to a 3 L 3 neck round bottom flask with overhead stirrer. The reaction mixture was stirred vigorously. After 2 hrs GCMS showed complete conversion to the epoxide (small aliquot removed from the reaction, diluted with an equal volume of $CH_3CN$, filtered through disposable pipette with a cotton plug). The colorless reaction was diluted with $CH_2Cl_2$ (1 L), brine (800 ml) and water (200 ml). The aqueous layer was extracted with additional $CH_2Cl_2$ (250 ml). The combined organic layers were washed with brine (4×200 ml), dried ($MgSO_4$) and evaporated (bath temp 45° C.) to a colorless oil (136 g, quantitative); $^1H$ NMR (500 MHz, DMSO-$d_6$) δ 8.35 (s, 1H), 7.78 (d, 2H, J=8.2 Hz)), 7.53 (d, 2H, J=8.2 Hz), 3.89 (ddd, 1H, J=13 Hz, J=3.5 Hz, J=1.6 Hz), 3.55 (ddd, 1H, J=13 Hz, J=6.1 Hz, J=1.3 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 8.98 min (m/e 194).

Example 32

(S)-5-(Chloromethyl)-3-[3-fluoro-4-(4-morpholinyl)phenyl]-2-oxazolinone. Anhydrous LiBr (345 mg, 4 mmol), and tri-n-butylphosphine oxide (980 mg, 4.5 mmol) were quickly added to a 250 ml 3 neck round bottom flask containing o-xylene (65 ml) that was outfitted with a 125 ml side arm dropping funnel and reflux condenser with an argon inlet valve on top and a football stirring bar. The mixture was refluxed for 30 minutes with stirring to dissolve the LiBr by distilling off a few mls of the xylene. A solution of freshly prepared 3-fluoro-4-morpholinophenylisocyanate (14.6 g, 66 mmol) and (S) epichlorohydrin (6 g, 5.0 ml, 66 mmol) (Atlantic SciTech Group, Inc) (98% purity) in o-xylene (35 ml) was placed in the dropping funnel and added to the reaction that had just been removed from the oil bath with stirring at such a rate that the reaction resumed refluxing. After complete addition, the light pink-brown reaction (that contained a small amount of insoluble material) was placed back in the oil bath and heated at reflux an additional 45 minutes, cooled to room temperature and filtered through fluted filter paper into a dropping funnel. The light brown solution was added in a slow stream to a stirring solution of hexane (500 ml). The resulting precipitate turned into a semi solid that solidified to an off-white crystalline solid after stirring overnight at room temperature. The solid was collected by filtration, washed with hexane and air dried (15.9 g, 77%). Recrystallization from 95% ethanol (150 ml) provided a light pink crystalline solid (12.85 g, 62%) after drying in vacuo at 55° C. LCMS: Retention time 8.16 min (85.3%) (m/e 315, MH+), 8.42 min (14.7%) (m/e 361, MH+ for the bromomethyl analog). $^1$H NMR (500 MHz, CDCl$_3$) δ 7.44 (dd, 1H, J=2.6 Hz, J=14.3 Hz), 7.14 (ddd, 1H, J=8.9 Hz, J=2.5 Hz, J=1.0 Hz), 6.95 (t, 1H, J=9.1 Hz), 4.84 (m, 1H), 4.13 (t, 1H, J=4.25 Hz), 3.92 (dd, 1H, J=5.65 Hz, J=9.1 Hz), 3.87 (t, 4H, J=4.6 Hz), 3.79 (dd, 1H, J=4.0 Hz, J=11.65 Hz), 3.75 (dd, 1H, J=6.6 Hz, J=11.65), 3.06 (t, 4H, J=4.6 Hz).

Example 33

(S)-5-(Azidomethyl)-3-[3-fluoro-4-(4-morpholinyl)phenyl]-2-oxazolinone. (S)-5-(Chloromethyl)-3-[3-fluoro-4-(4-morpholinyl)phenyl]-2-oxazolinone (9.88 g, 30.7 mmol), sodium azide (6.5 g, 100 mmol) and dimethylformamide (150 ml) were combined in a 500 ml round bottom flask with football stirring bar under argon and heated in an oil bath at 90° C. for 15 hrs. The light pink reaction mixture was cooled to room temperature and diluted with ethyl acetate (200 ml) and brine (200 ml). The lower organic layer was separated and the aqueous layer extracted with additional ethyl acetate (50 ml). The combined organic layers were washed with brine (3×100 ml), dried (MgSO$_4$) and evaporated to a light colored oil. The oil was diluted with ethanol (75 ml) resulting in the formation of a mass of white crystals. The crystals were cooled in an ice bath and were collected by filtration washing with cold ethanol providing 7.97 g (82%) of the title azide after drying in a vacuum oven at 50° C. LCMS: Retention time 8.15 min (100%) (m/e 322, MH+). $^1$H NMR (500 MHz, CDCl$_3$) δ 7.44 (dd, 1H, J=2.6 Hz, J=14.3 Hz), 7.13 (ddd, 1H, J=0.7 Hz, J=2.6 Hz, J=8.8 Hz), 6.94 (t, 1H, J=9.0 Hz), 4.77 (m, 1H), 4.05 (t, 1H, J=8.9 Hz), 3.87 (t, 4H, J=4.6 Hz), 3.82 (dd, 1H, J=6.2 Hz, J=8.9 Hz), 3.70 (dd, 1H, J=4.5 Hz, J=13.2 Hz), 3.59 (dd, 1H, J=4.5 Hz, J=13.2 Hz), 3.06 (t, 4H, J=4.7 Hz).

Example 34

(R)-N-[[3-(3-Fluoro-4-morpholinylphenyl)-2-oxo-5-oxazolidyl]methyl]acetamide, (R)-Linezolid. (S)-5-(Azidomethyl)-3-[3-fluoro-4-(4-morpholinyl)phenyl]-2-oxazolinone (7.8 g, 24.3 mmol) and thioacetic acid (20 ml) were combined in a 100 ml round bottom flask with stirring bar, fitted with a glass stopper and the resulting light yellow solution was stirred for 15 hrs at room temperature. The reaction mixture, containing a white precipitate, was warmed in a 50° C. water bath and a stream of nitrogen was blown into the reaction mixture with stirring until the solvent was removed. The white precipitate was treated with ethyl acetate (20 ml) and the mixture was heated to reflux and an equal volume of refluxing hexane was added. The crystalline mixture was cooled in an ice bath and the white solid was collected by filtration and washed with cold ethyl acetate:hexane (1:1) (6.5 gm, 79%). Recrystallized by dissolving in refluxing ethyl acetate (175 ml) and refluxed down to a volume of 75 ml with stirring. At a volume of ~150 ml white crystals started to form. The crystalline mixture was cooled in an ice bath and the shiny light pink crystals were collected by filtration and washed with cold ethyl acetate-hexane (1:1) (5.4 g, 66%) after drying in a vacuum oven at 50° C. $^1$HNMR (500 MHz, DMSO-d$_6$) δ 8.24 (t, 1H, J=5.8 Hz), 7.49 (dd, 1H, J=15.0 Hz, J=2.6 Hz), 7.17 (dd, 1H, J=8.8 Hz, J=2.3 Hz), 7.06 (t, 1H, J=9.5 Hz), 4.70 (m, 1H), 4.08 (t, 1H. J=9.0 Hz), 3.74 (t, 4H, J=4.5 Hz), 3.70 (dd, 1H, J=10.6 Hz, 6.4 Hz), 3.40 (t, 1H, J=5.5 Hz), 2.96 (t, 4H, J=4.6 Hz), 1.83 (s, 3H). Chiral chromatography: Retention time 13.2 min (5%) (m/e 338, MH+ for (S)-Linezolid), 14.05 min (95%) (m/e 338, MH+ for (R)-Linezolid), ee 90%. Chiral chromatography was carried out as follows: Column: Chiralcel OJ (Lot No. 168-053-40615) (Daicel Chemical Indust.) 250× 4.6 mm Cellulose-tris (4-methylbenzoate) coated with 10 um silica gel; Solvents A and B are as described under the "General" Example above; Method: Time 0 min: 20% B, Time 60 min 100% B, Gradient elution flow rate 1.00 ml/min.

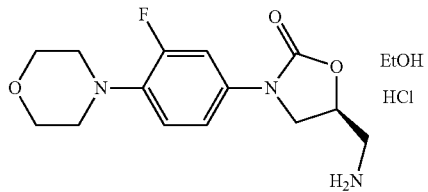 [SMILES: "EtOH" ; NC[C@H]1CN(c2ccc(N3CCOCC3)c(F)c2)C(=O)O1 ; Cl]

Example 35

(S)-N-[3-(3-Fluoro-4-morpholinylphenyl)-2-oxo-5-oxazolidyl]methylamine hydrochloride monoalcoholate. (S)-(E,Z)-5-((4-Chlorobenzylideneamino)methyl)-3-(3-fluoro-4-morpholinophenyl)oxazolidin-2-one (17 gm, 40.45 mmol), was added to a two phase solution of methylene chloride (85 ml), water (85 ml) and 12 N HC (7 ml) in a 500 ml round bottom flask with football stirring bar. The reaction mixture was rapidly stirred at room temperature forming a two-phase solution. After 30 minutes the organic layer was separated and the aqueous layer was extracted with methylene chloride (2×30 ml). The aqueous layer was basified to pH 8 to 9 with 10% aq. NaOH and cooled in an ice bath yielding white crystals. The crystals were collected by filtration and washed with cold water (2×25 ml). The crystals were air dried a few minutes on a Buchner funnel and were converted to the hydrochloride salt by dissolving in ethanol (700 ml) containing 10 N ethanolic HCl (10 ml), refluxing down to 200 ml yielding a mass of white crystals. The crystals were cooled in an ice bath, collected by filtration and washed with cold ethanol (12.0 gm, 89.5%) after drying in the vacuum oven at 50° C. LCMS: Retention time 4.69 min (100%) m/e 296 (MH$^+$), 613 ([2M+Na]$^+$). $^1$HNMR (500 MHz, DMSO-d$_6$) δ 8.36 (br s, 3), 7.49 (dd, 1H, J=2.55 Hz, J=14.95 Hz), 7.18 (dd, 1H, J=2.0 Hz, J=8.8 Hz), 7.07 (t, 1H, J=9.1), 4.94 (m, 1H), 4.16 (t, 1H, J=9.15 Hz), 3.85 (dd, 1H, J=6.6 Hz, J=9.23 Hz), 3.74 (t, 4H, J=4.6 Hz), 3.70 (br s, 6H), 3.44 (1EtOH CH$_2$, 2H, 7.0 Hz), 3.23 (m, 2H), 2.97 (t, 4H, J=4.6 Hz), 1.05 (1EtOH CH$_3$, 3 H, J=7.0 Hz).

Example 36

Recrystallization of linezolid (9) from ethyl acetate and hexane. Linezolid was recrystallized using a procedure similar to the one described by Brickner, S. J., et al., *J. Med. Chem.*, 1996, 39, 673-679. Thus, linezolid (1.05 g) was dissolved in refluxing ethyl acetate (utilizing a boiling stick) (25 ml) (required this amount of solvent to obtain a homogeneous clear colorless solution) and refluxing hexane (12 ml) was added all at once yielding a clear gently boiling solution. Within 30 seconds shiny white crystals started to form in the refluxing solution. The mixture was stirred and the Erlenmeyer flask filled with white fluffy crystals over ca. a minute or two. The flask was allowed to stand and slowly cool to room temperature over 30 minutes. The crystals were collected by filtration, washed with room temperature ethyl acetate:hexane (1:1) (10 ml), air dried in the Buchner funnel for 15 minutes and then in the vacuum oven for 1.5 hour at 35° C. (0.96 g).

The following publications, and each additional publication cited herein, are incorporated herein by reference in their entirety.
CN 101220001.
Heteroatom Chem 2008, 19, 316-9.
Tetrahedron Letters 2008, 49, 3060-62.
WO 200711684.
Tetrahedron Letters 2006, 47, 6799-680.
WO 2006091848.
WO 2006091731.
IN 2001MA00519.
WO 2006008754.
WO 2005099353.
Tetrahedron Letters 1999, 40, 4855-6.
WO 9924393.
Fujisaki, F.; Abe, N.; Sumoto, K. *Heterocycles* 2008, 75, 1681-1694.
Sridhar, R.; Perumal, P. T. *Syn. Comm.* 2003, 33, 607-611.
Brickner, S. J., et al., J. Med. Chem., 1996, 39, 673-679.
Maccaroni, E., et al., Inter. J. Pharmaceutics, 2008, 351, 144-151.
WO 2001057035.

What is claimed is:

1. A process for preparing linezolid or a pharmaceutically acceptable salt thereof, the process comprising:
   (a) mixing 3-fluoro-4-(morpholino)benzoyl azide with an oxirane of the formula,

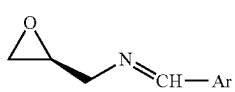

in the presence of catalytic amounts of anhydrous lithium bromide and tri-n-butylphosphine oxide to prepare a compound of the formula A,

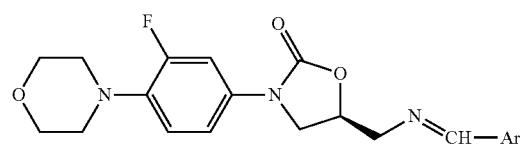

or a salt thereof; wherein Ar is optionally substituted phenyl; followed by (b) mixing a compound of the formula A in the presence of an acid to prepare a compound of formula B,

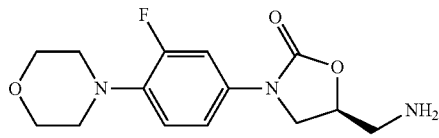

or a salt thereof; and followed by
   (c) mixing a compound of the formula B with an acetic anhydride to prepare a compound of formula C,

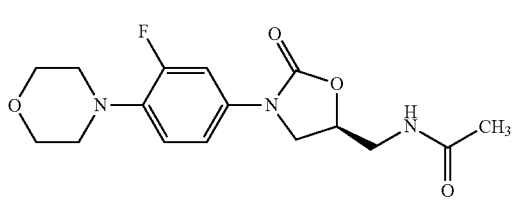

or a pharmaceutically acceptable salt thereof.

2. The process of claim 1, wherein step (a) is carried out in the presence of o-xylene.

3. The process of claim 2, wherein step (a) is carried out at reflux.

4. The process of claim 2, wherein step (a) is carried out under an inert atmosphere.

5. The process of claim 4, wherein the inert atmosphere is an argon atmosphere.

6. The process of claim 1, wherein the acid in step (b) is aqueous hydrochloric acid.

7. The process of claim 1, wherein the acid in step (b) is mixed in the presence of a solvent.

8. The process of claim 7, wherein the solvent is dichloromethane.

9. The process of claim 1, wherein the acid in step (b) is mixed in a 1:1 ratio of dichloromethane and water.

10. The process of claim 1, wherein the acid in step (b) is mixed at room temperature.

11. The process of claim 1, wherein step (c) is carried out in a two-phase solution.

12. The process of claim 11, wherein the two-phase solution comprises dichloromethane.

13. The process of claim 11, wherein step (c) is carried out at a pH of about 7.

14. The process of claim 1, wherein Ar is phenyl.

15. The process of claim 1, wherein Ar is 4-chlorophenyl.

16. The process of claim 1, further comprising crystallizing the compound of formula C.

17. The process of claim 16, wherein the crystallizing is carried out in the presence of ethyl acetate.

18. The process of claim 16, wherein the crystallizing comprises cooling a crystallization mixture in an ice bath.

19. The process of claim 1, wherein step (b) comprises quenching with aqueous sodium hydroxide.

20. The process of claim 1, wherein step (c) comprises quenching with aqueous sodium hydroxide.

* * * * *